(12) United States Patent
Zhang et al.

(10) Patent No.: US 9,746,434 B2
(45) Date of Patent: Aug. 29, 2017

(54) METHOD AND SYSTEM FOR DETERMINING FLOW DISTRIBUTION THROUGH A COMPONENT

(71) Applicants: Yibing Zhang, Annandale, NJ (US); Limin Song, West Windsor, NJ (US); Geoff Keiser, Morris Plains, NJ (US); Michael L. Hergenrother, Kingwood, TX (US); Berne K. Stober, Esmont, VA (US); Patricia H. Kalamaras, Milford, NJ (US); Benjamin S. Umansky, Fairfax, VA (US)

(72) Inventors: Yibing Zhang, Annandale, NJ (US); Limin Song, West Windsor, NJ (US); Geoff Keiser, Morris Plains, NJ (US); Michael L. Hergenrother, Kingwood, TX (US); Berne K. Stober, Esmont, VA (US); Patricia H. Kalamaras, Milford, NJ (US); Benjamin S. Umansky, Fairfax, VA (US)

(73) Assignee: EXXONMOBIL RESEARCH AND ENGINEERING COMPANY, Annandale, NJ (US)

( * ) Notice: Subject to any disclaimer, the term of this patent is extended or adjusted under 35 U.S.C. 154(b) by 277 days.

(21) Appl. No.: 14/226,997

(22) Filed: Mar. 27, 2014

(65) Prior Publication Data
US 2014/0294041 A1    Oct. 2, 2014

Related U.S. Application Data

(60) Provisional application No. 61/806,087, filed on Mar. 28, 2013.

(51) Int. Cl.
*G01N 25/18*    (2006.01)
*G01F 1/688*    (2006.01)
(Continued)

(52) U.S. Cl.
CPC ............ *G01N 25/18* (2013.01); *G01F 1/661* (2013.01); *G01F 1/684* (2013.01); *G01F 1/6884* (2013.01);
(Continued)

(58) Field of Classification Search
CPC ........ G01F 1/6884; G01F 1/684; G01F 1/661; G01N 25/18
See application file for complete search history.

(56) References Cited

U.S. PATENT DOCUMENTS

| 3,396,100 A | 8/1968 | Pettefer |
| 3,667,285 A | 6/1972 | Wright et al. |

(Continued)

FOREIGN PATENT DOCUMENTS

| DE | 10149092 A1 | 4/2003 |
| DE | 102004031324 A1 | 1/2006 |

(Continued)

OTHER PUBLICATIONS

Zhang, Yibing et al., "Applications of Optical Fiber Sensors in the Oil Refining and Petrochemical Industries," IEEE, 2011, pp. 246-249.

(Continued)

*Primary Examiner* — Paul West
(74) *Attorney, Agent, or Firm* — Chad A. Guice; Jamie L. Sullivan; Andrew T. Ward

(57) ABSTRACT

Systems and methods for determining the flow distribution of a fluid through a component with a sensing cable including an optical fiber sensor array aligned with a heating element disposed in the component. An excitation source is configured to propagate at least one heat pulse through the heating element along at least a portion of the sensing cable to affect an exchange of thermal energy between the heating element and the fluid exposed to the sensing cable. An (Continued)

optical signal is adapted to receive a signal from each of a plurality of sensor locations and measure a temperature profile corresponding to the heat pulse at the sensor locations. A control unit is configured to determine a flow of the fluid by determining one or more properties of the fluid exposed to the sensing cable at each of the plurality of sensor locations based on the temperature profile corresponding thereto. The present invention can be effective in accurate and high spatial resolution of flow distributions through vessel components, such as a particulate bed (such as a reactor catalyst bed), a wash bed including packing material, an absorbent bed, a structured bed, a filter, or the like.

37 Claims, 10 Drawing Sheets

(51) Int. Cl.
  *G01F 1/66* (2006.01)
  *G01F 1/684* (2006.01)
  *G01N 25/00* (2006.01)
  *G01K 11/32* (2006.01)
  *G01F 1/74* (2006.01)
(52) U.S. Cl.
  CPC ............ *G01F 1/74* (2013.01); *G01K 11/3206* (2013.01); *G01N 25/00* (2013.01)

(56) References Cited

U.S. PATENT DOCUMENTS

| | | | |
|---|---|---|---|
| 4,200,550 | A | 4/1980 | Scherrer et al. |
| 4,529,029 | A | 7/1985 | Block |
| 4,628,743 | A | 12/1986 | Miller, Jr. et al. |
| 4,722,781 | A | 2/1988 | Swartz et al. |
| 4,824,555 | A | 4/1989 | Paspek et al. |
| 4,938,876 | A | 7/1990 | Ohsol |
| 5,219,471 | A | 6/1993 | Goyal et al. |
| 5,712,275 | A | 1/1998 | Van Gestel |
| 5,882,506 | A | 3/1999 | Ohsol et al. |
| 6,450,257 | B1* | 9/2002 | Douglas .................. E21B 43/02 166/250.01 |
| 6,581,445 | B1 | 6/2003 | Weiss |
| 6,633,625 | B2 | 10/2003 | Jackson et al. |
| 6,853,798 | B1 | 2/2005 | Weiss |
| 7,240,547 | B2 | 7/2007 | Brown |
| 7,261,805 | B2 | 8/2007 | Grove et al. |
| 7,731,421 | B2 | 6/2010 | Hadley et al. |
| 7,886,109 | B2 | 2/2011 | Yamamoto et al. |
| 8,123,400 | B2 | 2/2012 | Andrejco et al. |
| 8,303,804 | B2 | 11/2012 | Helton et al. |
| 8,346,492 | B2 | 1/2013 | Yang et al. |
| 8,584,519 | B2 | 11/2013 | Maida et al. |
| 9,074,921 | B1 | 7/2015 | Parker, Jr. et al. |
| 2003/0094281 | A1 | 5/2003 | Tubel |
| 2004/0037752 | A1 | 2/2004 | Herzog |
| 2005/0011199 | A1 | 1/2005 | Grisham et al. |
| 2005/0247446 | A1* | 11/2005 | Gawthrop .............. B60H 1/004 165/202 |
| 2006/0010973 | A1 | 1/2006 | Brown |
| 2006/0214098 | A1* | 9/2006 | Ramos .................... E21B 47/09 250/256 |
| 2007/0158064 | A1* | 7/2007 | Pribnow ............... G01F 1/6884 166/250.01 |
| 2007/0234788 | A1 | 10/2007 | Glasbergen et al. |
| 2008/0128069 | A1* | 6/2008 | Sakrowski ............... C09D 5/16 156/71 |
| 2008/0130707 | A1 | 6/2008 | Yamamoto et al. |
| 2008/0239468 | A1 | 10/2008 | Hamada |
| 2008/0317095 | A1 | 12/2008 | Hadley et al. |
| 2009/0007652 | A1 | 1/2009 | Childers |
| 2009/0322544 | A1 | 12/2009 | McDowell |
| 2010/0247027 | A1 | 9/2010 | Xia et al. |
| 2012/0024758 | A1 | 2/2012 | Love |
| 2012/0080357 | A1 | 4/2012 | Novak et al. |
| 2013/0072739 | A1 | 3/2013 | Ruettinger et al. |
| 2013/0125643 | A1 | 5/2013 | Batty et al. |
| 2014/0290335 | A1* | 10/2014 | Shanks ............... E21B 47/1005 73/25.05 |
| 2014/0290343 | A1 | 10/2014 | Kulkarni et al. |
| 2014/0290357 | A1 | 10/2014 | Zhang et al. |
| 2014/0294040 | A1 | 10/2014 | Zhang et al. |
| 2014/0294041 | A1 | 10/2014 | Zhang et al. |
| 2015/0177042 | A1 | 6/2015 | Song et al. |
| 2015/0268078 | A1 | 9/2015 | Zhang et al. |

FOREIGN PATENT DOCUMENTS

| | | |
|---|---|---|
| GB | 2484990 A | 5/2012 |
| GB | 2496863 A | 5/2013 |
| WO | 03050576 A1 | 6/2003 |
| WO | 2005064117 A1 | 7/2005 |
| WO | 2008116069 A1 | 9/2008 |

OTHER PUBLICATIONS

Courivaud, R et al., "Fiber optics based monitoring of levees and embankment dams," 2011, 31st Annual USSD Conference, San Diego, California.

Sanders, Paul et al., "Recent Developments in Fiber Optic Sensor Technology for High Temperature Well Monitoring," 2009, GRC Annual Meeting—Reservoir Engineering.

International Search Report and Written Opinion PCT/US2014/032127 dated Jul. 29, 2014.

International Search Report and Written Opinion PCT/US2014/032131 dated Jul. 30, 2014.

International Search Report and Written Opinion PCT/US2014/032134 dated Sep. 3, 2014.

* cited by examiner

METHOD AND SYSTEM FOR DETERMINING FLOW DISTRIBUTION THROUGH A COMPONENT

CROSS-REFERENCE TO RELATED APPLICATIONS

This application claims priority to U.S. Provisional Application Ser. No. 61/806,087 filed Mar. 28, 2013, which is herein incorporated by reference in its entirety.

FIELD

The presently disclosed subject matter relates to methods and systems for determining the flow distribution of a fluid through a component. More particularly, the presently disclosed subject matter relates to determining the flow distribution of a fluid/gas through a component using a sensing cable including an optical fiber sensor array aligned with a heating element.

BACKGROUND

Components of certain equipment, such as that used in the petroleum and petrochemical industry, which includes the exploration, production, refining, manufacture, supply, transport, formulation or blending of petroleum, petrochemicals, or the direct compounds thereof, are often monitored to maintain reliable operation. However, such components can involve harsh conditions, such as high temperature, high pressure, and/or a corrosive environment, making it difficult or costly to obtain reliable measurements.

Determining flow distribution in refinery components or the like can facilitate the identification of hot spots, maldistribution, and other undesirable conditions. For example, monitoring hot spots and liquid maldistribution through a particulate bed, such as a reactor catalyst bed, an adsorbent bed, or a structured bed, can allow operators to take timely actions to avoid problematic conditions. For example, detecting a localized hot spot in a particulate bed in a fixed bed hydrotreating reactor, fixed bed hydrocracking reactor, or a vacuum tower wash section, can allow operators to avoid undesirable conditions in exothermic reactions. Additionally, monitoring liquid/gas flow distribution in a fixed reactor bed can be contribute to ensuring optical operation of the reactor, and can allow operators to alter the flow to increase utilization of the bed, increase the run-length, and thus enhance operations.

Conventional techniques for monitoring temperature distribution and flow of a fluid, such as for detection of hot spots and maldistribution, often rely on multiple thermocouples to monitor temperature distribution, e.g., inside fixed bed reactors. However, the number of thermocouples used for hot-spot detection within a particulate can be limited by the space inside the bed and the cost of installation and maintenance. Thus it can be difficult to provide adequate coverage inside the fixed bed space for hot spot detection. In addition, the temperature distribution measurement is an indirect indicator of the flow distribution. Therefore, flow conditions inferred from the limited point temperature measurements provided by thermocouples, constrained by the physical size of the thermocouples as well as the cost of installation and maintenance, can be inaccurate and unreliable.

Certain distributed optical fiber sensing technologies also have been proposed. However, the application of optical fiber sensors can be limited by harsh conditions, such as high temperature, high pressure and chemicals, such as hydrogen. For example, even special optical fibers and their protective coatings, such as those developed for down-hole applications, can be insufficient for long-term and reliable sensor deployment in more challenging environments, for example, in a hydrotreating or hydrocracking reactor. Furthermore, passive temperature measurements using distributed optical fiber sensors often involve low signal to noise ratio and provide only limited information about the properties of the surrounding media (i.e., the temperature at each sensor location at a given time). While additional properties of the surrounding media can in some circumstances, with suitable assumptions and boundary conditions, be inferred, such inferences are often inaccurate.

Accordingly, there is a continued need for improved techniques for determining the flow distribution of a fluid/gas through a component.

SUMMARY

The purpose and advantages of the disclosed subject matter will be set forth in and apparent from the description that follows, as well as will be learned by practice of the disclosed subject matter. Additional advantages of the disclosed subject matter will be realized and attained by the methods and systems particularly pointed out in the written description and claims hereof, as well as from the appended drawings. To achieve these and other advantages and in accordance with the purpose of the disclosed subject matter, as embodied and broadly described, the disclosed subject matter includes systems and methods for determining the flow distribution of a fluid through a component.

In accordance with one aspect of the disclosed subject matter, a method for determining the flow distribution of a fluid through a component includes providing within a component a sensing cable including an optical fiber sensor array aligned with a heating element. The method includes propagating at least one heat pulse through the heating element along at least a portion of the sensing cable to affect an exchange of thermal energy between the heating element and the fluid exposed to the sensing cable. The method includes measuring, over time, a temperature profile of the sensing cable corresponding to the heat pulse at each of a plurality of sensor locations on the optical fiber sensor array. The method includes determining a flow of the fluid by determining one or more properties of the fluid exposed to the sensing cable at each of the plurality of sensor locations based on the temperature profile corresponding thereto.

In certain embodiments, the component can include a particulate bed, a wash bed including packing material, an absorbent bed, a structured bed, or a filter. In an embodiment, the component is a hydroprocessing reactor (i.e., a reactor vessel for catalytically reacting a hydrocarbon in the presence of a catalyst and hydrogen) which includes a particulate bed, and the particulate bed is comprised of catalyst particles. In a preferred embodiment, such catalyst particles are comprised of a hydrodesulfurization catalyst (i.e., a catalyst effective for removing sulfur atoms/compounds from hydrocarbons), a hydrodenitrogenation catalyst (i.e., a catalyst effective for removing nitrogen atoms/compounds from hydrocarbons), a hydrodeoxygenation catalyst (i.e., a catalyst effective for removing oxygen atoms/compounds from hydrocarbons), a hydrocracking catalyst (i.e., a catalyst effective for cracking hydrocarbons into lower molecular weight compounds), a hydroreforming catalyst (i.e., a catalyst effective for producing aromatic hydrocarbon compounds from non-aromatic hydrocarbons), a hydroisomerization catalyst (i.e., a catalyst effective for producing iso-paraffinic compounds from non-iso-paraffinic hydrocarbons), or any combination thereof. As embodied herein, measuring the temperature profile corresponding to the heat pulse at each of the plurality of sensor locations can include, for each sensor location, measuring a plurality of temperatures over a period of time upon arrival of the heat pulse at the sensor location. Determining the flow of the fluid can include, for each temperature profile, performing a regression of the plurality of temperatures over a logarithm of corresponding measurement times for a predetermined time window in the period of time to generate a slope and an intercept of the regression, wherein the slope and the intercept relate to the flow of the fluid over the sensing cable at the sensor location. Additionally or alternatively, determining the flow of the fluid can include, for each temperature profile, generating a time derivative by calculating a derivative of the plurality of temperature measurements with respect to time, applying a transform to the time derivative to generate a complex spectrum, and determining an amplitude and a phase of the complex spectrum, wherein the amplitude and the phase of the complex spectrum relate to the flow of the fluid over the sensing cable at the sensor location. Determining the flow of the fluid can further include generating a frequency derivative spectrum by calculating the derivative of the complex spectrum with respect to frequency, and determining an amplitude and a phase of the frequency derivative spectrum, wherein the amplitude and the phase of the frequency derivative spectrum relate to the flow of the fluid over the sensing cable at the sensor location.

In certain embodiments, determining the flow of the fluid can include detecting a misdistribution condition in the component by monitoring the temperature profile corresponding to each of the plurality of sensor locations, and comparing the monitored temperature profiles to predetermined temperature profiles corresponding to a desired operation condition. Alternatively, determining the flow of the fluid further can include detecting a misdistribution condition in the component by monitoring a first temperature profile corresponding to each of the plurality of sensor locations and at least a second temperature profile corresponding to each of the plurality of sensor locations, and comparing the first and second temperature profiles to detect a change in operation condition.

In accordance with another aspect of the disclosed subject matter a system for determining the flow distribution of a fluid through a component includes a sensing cable including an optical fiber sensor array aligned with a heating element disposed in the component, the optical fiber sensor array having a plurality of sensor locations. The system includes an excitation source coupled with the heating element and configured to propagate at least one heat pulse through the heating element along at least a portion of the sensing cable to affect an exchange of thermal energy between the heating element and the fluid exposed to the sensing cable. The system includes an optical signal interrogator coupled with the optical fiber sensor array and adapted to receive a signal from each of the plurality of sensor locations and configured to measure, over time, a temperature profile of the sensing cable corresponding to the heat pulse at each of the plurality of sensor locations on the optical fiber sensor array. The system includes a control unit, coupled with the heating element and the optical signal interrogator, to determine a flow of the fluid by determining one or more properties of the fluid exposed to the sensing cable at each of the plurality of sensor locations based on the temperature profile corresponding thereto.

In certain embodiments, the component can include a particulate bed, a wash bed including packing material, an absorbent bed, a structured bed, or a filter. As embodied herein, the optical signal interrogator can be configured, for each of the plurality of sensor locations, to measure a plurality of temperatures over a period of time upon arrival of the heat pulse at the sensor location. The control unit can be configured, for each temperature profile, to perform a regression of the plurality of temperatures over a logarithm of corresponding measurement times for a predetermined time window in the period of time to generate a slope and an intercept of the regression, wherein the slope and the intercept relate to the flow of the fluid over the sensing cable at the sensor location. Additionally or alternatively, the control unit can be configured, for each temperature profile, to generate a time derivative by calculating a derivative of the plurality of temperature measurements with respect to time, apply a transform to the time derivative to generate a complex spectrum, and determine an amplitude and a phase of the complex spectrum, wherein the amplitude and the phase of the complex spectrum relate to the flow of the fluid over the sensing cable at the sensor location. The control unit can be further configured to generate a frequency derivative spectrum by calculating the derivative of the complex spectrum with respect to frequency, and determine an amplitude and a phase of the frequency derivative spectrum, wherein the amplitude and the phase of the frequency derivative spectrum relate to the flow of the fluid over the sensing cable at the sensor location.

In certain embodiments, the control unit can be configured to detect a misdistribution condition in the component by monitoring the temperature profile corresponding to each of the plurality of sensor locations, and comparing the monitored temperature profiles to predetermined temperature profiles corresponding to a desired operation condition. Alternatively, the control unit can be further configured to detect a misdistribution condition in the component by monitoring a first temperature profile corresponding to each of the plurality of sensor locations and at least a second temperature profile corresponding to each of the plurality of sensor locations, and comparing the first and second temperature profiles to detect a change in operation condition.

It is to be understood that both the foregoing general description and the following detailed description are exemplary and are intended to provide further explanation of the disclosed subject matter claimed.

The accompanying drawings, which are incorporated in and constitute part of this specification, are included to illustrate and provide a further understanding of the disclosed subject matter. Together with the description, the drawings serve to explain the principles of the disclosed subject matter.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION

Figure 1A:
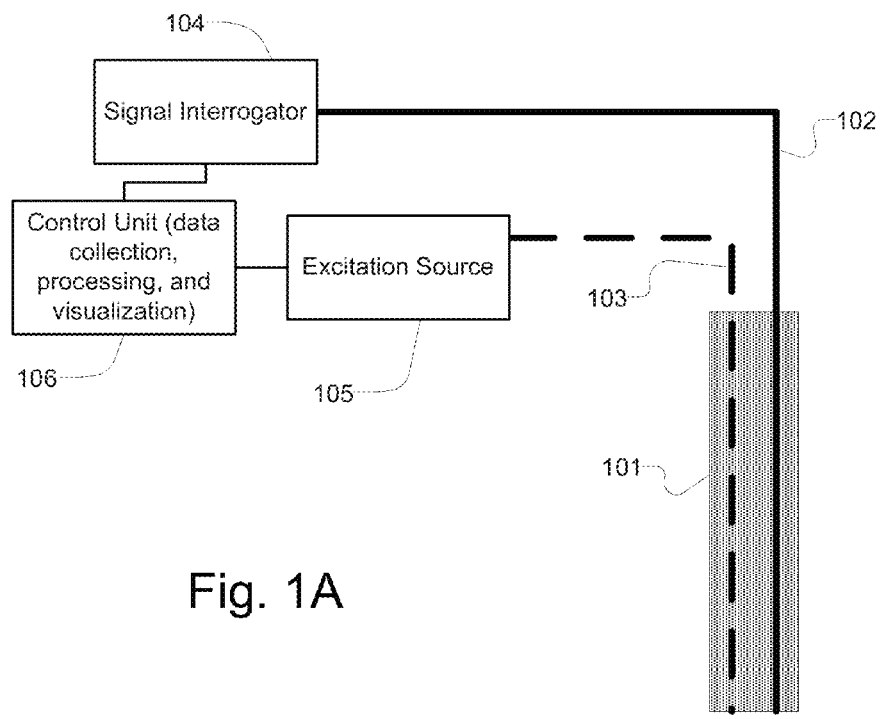
FIG. 1A is a schematic diagram of an exemplary sensing system in accordance with the disclosed subject matter.

As noted above and in accordance with one aspect of the disclosed subject matter, methods disclosed herein include determining the liquid/gas flow distribution of a fluid through a component with a sensing cable including an optical fiber sensor array aligned with a heating/cooling element. The method includes propagating at least one heating/cooling pulse through the heating/cooling element along at least a portion of the sensing cable to affect an exchange of thermal energy between the heating element and the fluid exposed to the sensing cable. The method includes measuring, over time, a temperature profile of the sensing cable corresponding to the heat pulse at each of a plurality of sensor locations on an optical fiber sensor array. The method includes determining a flow distribution of the fluid by determining one or more properties of the fluid exposed to the sensing cable at each of the plurality of sensor locations based on the temperature profile corresponding thereto.

Furthermore, systems for determining the flow distribution of a fluid through a component are also provided. Such systems include a sensing cable including an optical fiber sensor array aligned with a heating element disposed in the component, the optical fiber sensor array having a plurality of sensor locations. The system further includes an excitation source coupled with the heating element and configured to propagate at least one heat pulse through the heating element along at least a portion of the sensing cable to affect an exchange of thermal energy between the heating element and the fluid exposed to the sensing cable. The system also includes an optical signal interrogator coupled with the optical fiber sensor array and adapted to receive a signal from each of the plurality of sensor locations and configured to measure, over time, a temperature profile of the sensing cable corresponding to the heat pulse at each of the plurality of sensor locations on the optical fiber sensor array. A control unit, coupled with the heating element and the optical signal interrogator, determines a flow of the fluid by determining one or more properties of the fluid exposed to the sensing cable at each of the plurality of sensor locations based on the temperature profile corresponding thereto.

Reference will now be made in detail to the various exemplary embodiments of the disclosed subject matter, exemplary embodiments of which are illustrated in the accompanying drawings. The accompanying figures, where like reference numerals refer to identical or functionally similar elements, serve to further illustrate various embodiments and to explain various principles and advantages all in accordance with the disclosed subject matter. The accompanying figures, where like reference numerals refer to identical or functionally similar elements, serve to further illustrate various embodiments and to explain various principles and advantages all in accordance with the disclosed subject matter. For purpose of explanation and illustration, and not limitation, exemplary embodiments of the disclosed subject matter are shown in FIGS. 1-8.

In accordance with the disclosed subject matter, characteristics of one or more materials can be measured with the use of an optical fiber sensor array having a plurality of sensor locations aligned with a heating/cooling element in a sensing cable. At least one heating/cooling pulse is propagated through the heating/cooling element along at least a portion of the sensing cable to affect an exchange of thermal energy between the heating/cooling element and one or more media exposed to the sensing cable. A temperature profile of the sensing cable (e.g., in the time domain and/or spatial domain) corresponding to the heating/cooling pulse at the plurality of sensor locations on the optical fiber sensor array can be measured to support a variety of techniques in accordance with the disclosed subject matter.

Generally, for purpose of illustration and not limitation, thermal properties, such as material density, thermal conductivity, heat capacity, or heat diffusion coefficient, of one or more materials can be measured by generating a heat disturbance and sensing a temperature response. In like fashion, dynamic physical properties, such as the flow of a material, can also be measured. As disclosed herein, techniques for measuring temperature can include obtaining temperature measurements in both the temporal and spatial domain. For example, distributed temperature sensing (DTS) systems can provide temperature measurements along the length of a sensing cable continuously or at regular intervals. The change in these temperature measurements can correspond to certain properties of a surrounding material or materials.

For purpose of illustration, and not limitation, an exemplary system for measuring the characteristics of a material in accordance with an exemplary embodiment of the disclosed subject matter will be described. In general, with reference to FIG. 1A, an exemplary sensing system in accordance with the disclosed subject matter can include a sensing cable 101 having disposed therein a heating/cooling device 103 and optical fiber sensor array having a plurality of sensors 102. The sensing cable 101 can be operatively coupled with a control unit 106. For example, the heating/ cooling device 103 can be coupled with an excitation source 105, which in turn can be coupled with the control unit 106. Likewise, the optical fiber sensor array 102 can be coupled with a signal interrogator 104, which can be coupled with the control unit 106. Generally, uniform heat can be delivered (e.g., heat energy can be provided or absorbed) along the sensing cable 101 via the heating/cooling device 103 and the excitation source 105. A temperature profile or its variation with time (e.g., variation rate) can be measured using the optical fiber sensor array 102 and signal interrogator 104. The control unit 106 can be adapted to collect data, process data, and/or present data for visualization, for example via one or more displays (not shown).

The sensing cable 101 can be arranged in a variety of configurations. Two exemplary configurations are depicted in FIG. 1B and FIG. 1C, respectively. For example, FIG. 1B depicts a cross section of a sensing cable 101 with the heating/cooling device 103 and the optical fiber sensor array 102 arranged in parallel with each other. The sensing cable 101 can include, for example, an outer casing (not shown) optionally filled with a filler material 110 to maintain the heating/cooling device 103 and optical fiber sensor array 102 in place. Additionally or alternatively, the filler can be extended about the heating/cooling device 103 and temperature sensor 102 with or without the outer casing. The filler can be, for example, a material with high thermal conductivity, such as magnesium oxide (MgO). The outer casing can be a rigid and/or durable material, for example a metal tube. To ensure measurement accuracy, e.g., under harsh conditions, such as fouling or corrosion, the sensing cable 101 casing can be treated with a suitable coating, as described in more detail below. Alternatively, and as depicted in cross section in FIG. 1C, the heating/cooling device 103 and the temperature sensor array 102 can be generally coaxial with each other, wherein the heating/cooling device 103 is disposed concentrically around the temperature sensor array 102.

As embodied herein, the sensing cable 101 can be mineral insulated for protection of a optical fiber sensor array 102 including one or more optical fibers. The optical fibers can be coated and placed into a protective tube structure for enhanced mechanical integrity and resistance to adversary effects of environmental factors, such as $H_2$, $H_2S$ and moisture. The sensing cable 101 can further be protected using metal and mineral insulation material (e.g., MgO) for effective thermal conduction. The optical fibers can have a relatively small diameter, and thus can be placed into a protective tube with a relatively small diameter, allowing a faster thermal response and dynamic process monitoring. One of ordinary skill in the art will appreciate that the dimensions of the sensing cable 101 can be selected for a desired application. For example, if further protection from the local environment is desired, a sensing cable 101 with a larger diameter, and thus additional filler, can be selected.

Furthermore, a number of commercially available fibers for the temperature sensor 102 can be used, such as a Fiber Bragg Grating array, Raman scattering based sensor, Rayleigh scattering based sensor or Brillouin scattering based sensor. One of ordinary skill in the art will appreciate that each type of fiber sensor can have certain properties, such as response time, sensing resolution, immunity to hydrogen darkening, effective sensing cable length, and ability to sense temperature and/or strain, as illustrated for purpose of example and not limitation in Table 1. For example, a Fiber Bragg grating sensing system can include a relatively fast response time, high spatial resolution, and can be employed over a sensing cable length upwards of 100 km or longer in connection with the use of optical fiber amplifiers. Raman and Brillouin scattering sensing systems can have relatively low response times (e.g., on the order of several seconds), and spatial resolution on the order of centimeters. Rayleigh scattering sensing systems, when operated to sense temperature, can have a response time of several seconds with relatively high spatial resolution.

TABLE 1

| Sensor types | Fastest response time | Typical point sensor size (m) | Immunity to H2 darkening | Longest sensor cable length |
|---|---|---|---|---|
| Fiber Bragg Grating (FBG) | <10 ms | 0.01 | high | <100 km or longer |
| Raman scattering sensor | >Several seconds | 0.25~0.5 | low | <100 km |
| Rayleigh scattering sensor (Temp) | >Several seconds | 0.01 | low | <70 m |
| Rayleigh scattering sensor (Acoustic) | <1 ms | 0.5 | low | <100 km |
| Brillouin scattering sensor | >Several seconds | 0.1~50 | low | <100 km |

One of ordinary skill in the art will also appreciate that certain of the various types of sensing systems can be used to sense temperature and/or strain (e.g., to sense acoustics). For example, Fiber Bragg Grating sensing systems can be used to measure both temperature and strain, for purposes of sensing temperature and acoustics. Raman scattering sensing systems are typically used to sense temperature. Brillouin scattering sensing systems can be used to measure temperature and strain, and are typically used to sense temperature. Rayleigh scattering sensing systems can be used to measure temperature and strain, and can be used to sense either temperature or acoustics. One of ordinary skill in the art will appreciate that when Rayleigh scattering sensing systems are used to sense acoustics, response time can increase to lower than 1 ms and spatial resolution can increase to approximately 50 cm.

Referring again to FIG. 1A, and as noted above, the control unit 106 can be coupled with the signal interrogator 104. The signal interrogator 104 can be, for example, an optical signal interrogator. Various optical signal interrogators may be used, depending on the type of optical fiber sensing techniques to be employed. The controller 106 can be adapted to perform signal processing on real-time temperature data provided by the signal interrogator 104. For example, the control unit 106 can be adapted to identify and record continuous or repeated temperature measurements at each of a plurality of sensor locations along the sensing cable 101. Additionally, the control unit 106 can be adapted to process temperature measurements over time to identify a characteristic of the material surrounding the sensing cable at one or more sensor locations.

As disclosed herein, a variety of suitable methods can be employed for generating the heating/cooling pulse along the sensing cable 101. As used herein, the term "pulse" includes a waveform of suitable shape, duration, periodicity, and/or phase for the intended purpose. For example, and not limitation, and as described further below, the pulse may have a greater duration for one intended use, such as the determination of deposits, and a shorter duration for another intended use, such as the determination of flow. As embodied herein, the heating/cooling device 103 can be an electrically actuated device. For example, the heating/cooling device 103 can include a resistive heating wire, and the excitation source 105 can be electrically coupled with the heating wire and adapted to provide a current there through. Passing of a current through the resistive heating wire can provide thermal energy along the length of the sensing cable 101, thereby generating a uniform heating/cooling effect along the sensing cable. Alternatively, the heating/cooling device 103 can include a thermoelectric device, and can be likewise coupled to the excitation source 105. The thermoelectric device can use the Peltier effect to heat or cool a surrounding medium. That is, for example, the thermoelectric device can be a solid-state heat pump that transfers heat from one side of the device to the other. The thermoelectric device can be configured, for example, to provide heating to the optical fiber sensor for a certain polarity of electric potential and cooling for the opposite polarity. As disclosed herein, and for purpose of simplicity, the terms "heating/cooling device", and "heating/cooling pulse" will be referred to generally as a "heating device" or "heating element" and as a "heat pulse," respectively. Depending upon the context, such terms are therefore understood to provide heating, cooling, or both heating and cooling.

In an exemplary embodiment of the disclosed subject matter, the excitation source 105 can be configured to deliver current in a predetermined manner. For example, the excitation source 105 can be configured to generate pulses having predetermined wave forms, such as square waves, sinusoidal waves, or saw tooth waves. The excitation source 105 can be configured to generate the pulses at a predetermined frequency. For example, and not limitation, and with reference to FIG. 2, the excitation source 105 can be configured to generate an electric pulse of a rectangular wave form 210 through the heating/cooling element 103. The electric pulse can create a heat pulse 220 in the heating/cooling element 103 with the same wave form. That is, for example, the heat flow through the heating/cooling element 103 can be given by $I^2R/A$, where I is the current, R is the resistance of the heating/cooling element 103, and A is the surface area of a cross section of the heating/cooling element 103. The heat pulse can result in a heat exchange between the sensing cable 101 and the surrounding media. The temperature at each sensor location can be recorded to generate a "temperature profile" 230 for each sensor location. For example, the temperature at each sensor location can be recorded with a sampling frequency of 50 Hz. The temperature profile 230 can correspond to characteristics of the medium surrounding the sensing cable 101 at each sensor location.

For purposes of illustration, and not limitation, the underlying principles of thermally activated ("TA") measurement techniques will be described generally. Prior to heating or cooling by the heating/cooling device 103, temperature measurements of the surrounding medium can be taken with the optical fiber sensor array 102 of the sensing cable 101 and the temperature profile can be recorded as a reference. Due to the Joule effect, the heating device 103 can deliver a constant and uniform heat along the cable, heating up both cable and surrounding medium near the cable surface. For purposes of illustration, the temperature measured by the optical fiber can be described by the following equation:

$$\frac{\partial T}{\partial t} = \frac{1}{mc_p}(\dot{E}_{gen} - \dot{E}_{loss}), \quad (1)$$

where $\dot{E}_{gen}$ is the heat generation rate per unit length from the heating device, $\dot{E}_{loss}$ is the heat loss rate due to heat transfer from the sensing cable to the surrounding medium, and m and $c_p$ represent the mass and heat capacitance of the sensing cable per unit length. The heat generation within the sensing cable due to the Joule effect can be given by:

$$\dot{E}_{gen} \propto Zi^2, \quad (2)$$

where Z is the impedance of the sensing cable per unit length and the rate of heat loss from the sensing cable to the surrounding media can be decomposed into heat diffusion and heat convection (e.g., $\dot{E}_{loss}$ can include both heat diffusion (conduction) in a stationary medium and or convective heat transfer in a flowing medium):

$$\dot{E}_{loss} = \dot{E}_{diffusion} + \dot{E}_{convection} \quad (3)$$

For a stationary medium, the heat loss term can be given as:

$$\dot{E}_{loss} \propto Ak\Delta T, \quad (4)$$

where A is effective heat transfer area of the sensing cable, k is effective heat conduction coefficient of the medium and $\Delta T$ is the effective temperature gradient across the sensing cable and the medium.

The heat capacitance of the cable per unit length can limit the frequency of the thermal response of the cable, and thus the cable can be designed with a heat capacitance suited to the desired data frequency. Because heat generation can be relatively constant and uniform, the rate of change in localized temperature can depend primarily on the heat transfer between the cable and the surrounding medium. If the localized heat transfer is high at a particular point on the sensing cable, then the rate of change of temperature at that point along the cable, measured by one temperature sensor in the optical fiber, can be small. Otherwise, the temperature changing rate will be large. When subject to a heterogeneous medium or a mixed medium consisting of layers of different fluids or the like, the spatial distribution of the temperature along the sensor array can be indicative of the interface between the different media.

For purpose of illustration, and not limitation, transient temperature analysis techniques to determine characteristics of a medium will now be described with the sensing cable modeled as an infinitely long thin cylinder placed in an infinite homogeneous medium. For purposes of this description, it is assumed that at time zero (t=0) an electrical current, i, and the heat generation rate per length of the cylinder is given by:

$$q = \pi r_0^2 z_0 i^2, \quad (5)$$

where $r_0$ is the radius of the cylinder, and $z_0$ is the resistance of the cylinder per unit of volume. A closed form solution for the temperature on the surface of the cylinder can be given as:

$$T(r_0, t) - T_\infty = \frac{q}{4\pi k} \int_{\frac{r_0^2}{4\alpha t}}^{\infty} \frac{e^{-u}}{u} du, \quad (6)$$

where k and $\alpha$ are the heat conductivity and diffusivity coefficients of the medium, and $T_\infty$ is the initial temperature distribution along the sensing cable. The normalized temperature change and normalized time t can be defined as:

$$\Delta T^* = \frac{T(r_0, t) - T_\infty}{q/(4\pi k)} \quad (7)$$

and $$t^* = \frac{4\alpha t}{r_0^2}. \quad (8)$$

Equation 6 can thus be given as:

$$\Delta T^* = \int_{1/t^*}^{\infty} \frac{e^{-u}}{u} du. \quad (9)$$

The incomplete gamma function can have following expansion form for small but non-zero value of z (0<z<2.5):

$$\Gamma(z) = \int_z^{\infty} \frac{e^{-u}}{u} du = -\gamma - \ln(z) - \sum_{n=1}^{\infty} \frac{(-z)^n}{n(n!)}. \quad (10)$$

The temperature response as given by equation 6 above can be further approximated as $$\Delta T^* \approx -\gamma - \ln(1/t^*), \quad (11)$$

when $$z = 1/t^* \ll 1. \quad (12)$$

In accordance with this illustrative and non-limiting model, comparison of the normalized temperature change as a function of normalized time (e.g., as given by equation 9 and equation 11, respectively) indicates that when the normalized time is greater than approximately 10, equation 11 is a good approximation of normalized temperature change. Moreover, equation 11 above indicates that temperature change can increase linearly with the log of time when the heating time is sufficiently large so as to satisfy the criteria in equation 12. Thus, the equation can be written as:

$$\Delta T(r_0, t) \approx a + b \ln(t), \quad (13)$$

where parameters a and b are function of thermal properties of the medium for given heating rate, and are given by:

$$a = \frac{q}{4\pi k}\left(-\gamma - \ln\left(\frac{r_0^2}{4\alpha}\right)\right) \quad (14)$$

and $$b = \frac{q}{4\pi k}. \quad (15)$$

Thus, equation 13 can provide a theoretical basis for determining the thermal properties of a medium based on measurement of transient temperature. One of ordinary skill in the art will appreciate that continuous heating can consume more electrical energy and make measurements less sensitive to dynamic change of the thermal properties to be measured (e.g., when the medium mixture changes with time), and thus pulsed heating in accordance with the disclosed subject matter can provide benefits such as decreased electrical energy usage and for measurement of dynamic conditions of surrounding materials.

For purpose of illustration, and not limitation, an exemplary method of measuring the characteristics of the media surrounding the sensing cable using thermal analysis sensing techniques will be described. In general, an optimized waveform of electrical pulse (for example, a square wave) can be delivered along the length of the heating/cooling device 103, and temperature can be monitored using a temperature sensor array 102, e.g., optical fiber sensors. Owing to the uniformity of the heating/cooling effect along the sensing cable, temperature readings can vary depending on localized heat transfer process, which can be a function of the thermal properties (e.g., thermal conductivity, heat capacity) and physical conditions (static or flow) of the medium surrounding the sensing cable 101. The control unit 106 can be adapted to determine the characteristics of the surrounding media simultaneously, using the temperature profile.

A single heating pulse (e.g., arising from an optimized waveform of electrical pulse) can create a temperature response which can be derived in accordance with the exemplary and non-limiting model described herein using superposition as follows:

$$T(r_0, t) - T_\infty = \frac{q}{4\pi k}\left(\int_{\frac{r_0^2}{4\alpha t}}^{\infty} \frac{e^{-u}}{u} du - \int_{\frac{r_0^2}{4\alpha(t-t_0)}}^{\infty} \frac{e^{-u}}{u} du\right). \quad (16)$$

The first term in the bracket of equation 16 can represent the heating from t to $t_0$, and the 2nd term the cooling after $t_0$. Data collected during heating and cooling are analyzed separately, as disclosed herein, to derivate estimates of thermal properties of the medium.

Based upon the above, the control unit 106 can be adapted to determine the characteristics of the surrounding media using a variety of suitable techniques. For example, the temperature profile at each sensor location can be used to determine the characteristics of the surrounding media directly. The temperature measurements during heating and/or cooling of the sensing cable, corresponding to the timing of the rectangular electrical pulse, can be used to generate a feature-temperature profile at each sensor location. For example, the feature-temperature profiles can be extracted from the temperature data at distinctive conditions: heating (e.g., the condition during which the heat pulse is passing over a sensor location), cooling (e.g., the condition during which the heat pulse has passed over the sensor location and heat is being exchanged between the sensing cable and the surrounding media) and peak temperature (e.g., approximately the maximum temperature recorded at the sensor location for each heat pulse).

Figure 3:
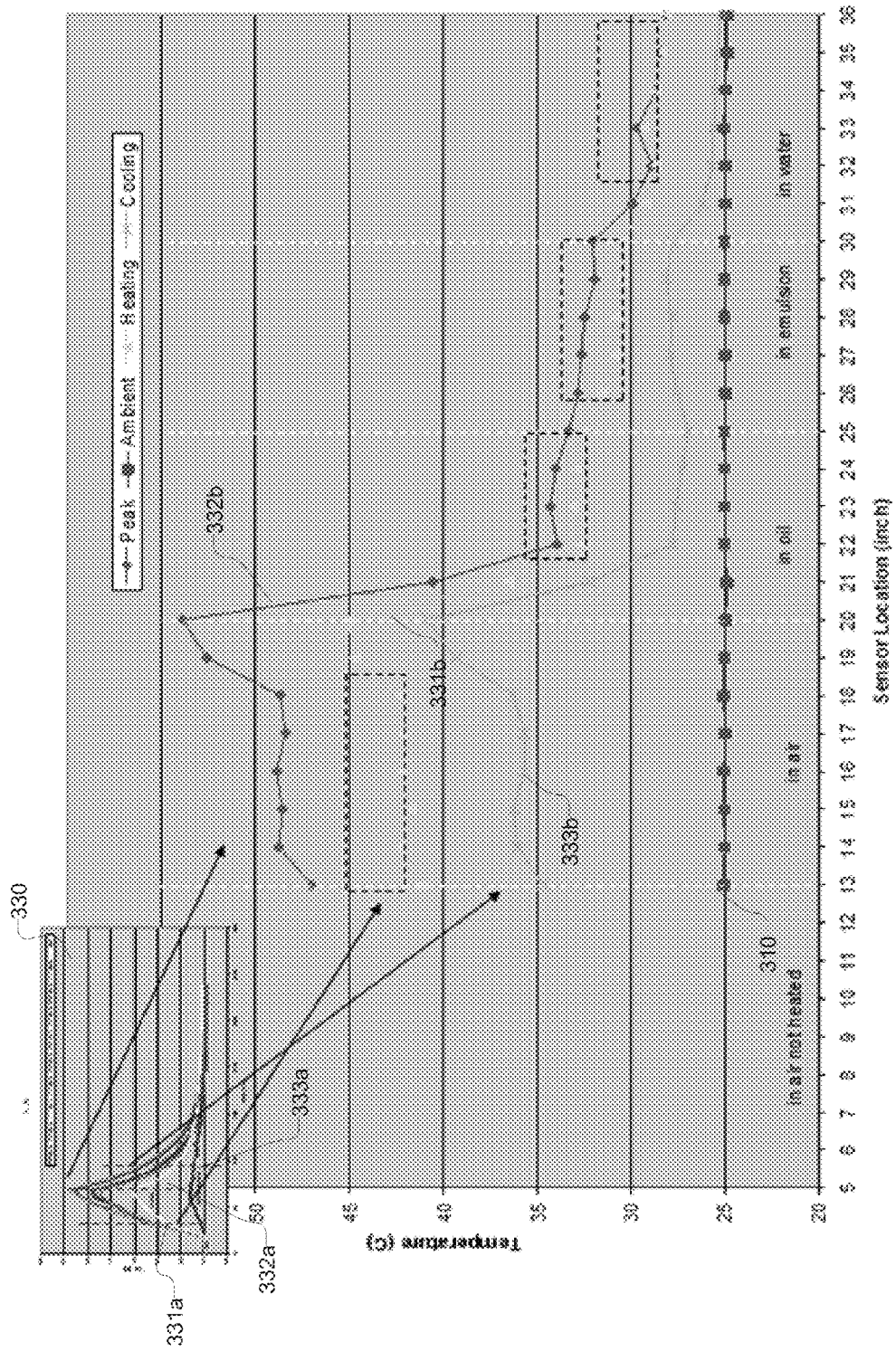
FIG. 3 is a graph illustrating a direct temperature sensing technique for a plurality of sensor locations in accordance with the disclosed subject matter.

For purpose of illustration, and not limitation, and with reference to FIG. 3, the control unit 106 can be configured to determine temperature characteristics of surrounding media using the feature-temperature profile at each sensor location. FIG. 3 shows distribution of feature temperatures along a sensing cable exposed to different media at different sensor locations. Graph 330 depicts the measured temperature profiles for a plurality of sensor locations. In accordance with the disclosed subject matter, feature-temperatures 331b, 332b, and 333b can be extracted from the measured temperature profile depicted in graph 330. For example, at each sensor location, feature-temperature 331b can correspond to a heating condition (e.g., while the heat pulse is passing over the sensor location), and can be extracted for each sensor location at a corresponding time 331a. Likewise, feature-temperature 332b can correspond to a peak temperature, and can be extracted for each sensor location at a corresponding time 332a. Similarly, feature temperature 333b can correspond to a cooling condition (e.g., after the heat pulse has passed over the sensor location and during which heat exchange between the cable and the surrounding media takes place) and can be extracted for each sensor location at a corresponding time 333a. Temperature 310 is the measured temperature at each sensor location during ambient conditions (e.g., no heat is applied).

As illustrated by FIG. 3, the feature temperature at each sensor location can correspond to the temperature characteristics of the surrounding media. For example, as depicted in FIG. 3, a 36 inch sensing cable arranged in a vertical configuration with a sensor disposed or located each unit inch along the cable can be exposed to a stack of air, oil, emulsion, and water. It should be noted that FIG. 3 depicts data from 24 sensor locations. Assuming each medium is stationary around the sensing cable, the rate of heat exchange, and thus the feature-temperature profiles 331b, 332b, and 333b, between the sensing cable and the surrounding media at each sensor location can correspond to the heat conduction of the surrounding media. That is, for example, heat transfer between the sensing cable and surrounding air can be lower than that between the sensing cable and water, as water has a higher heat conduction. Oil and emulsion layers can also be identified in this manner.

The determination of the characteristics of the media surrounding the sensing cable can be achieved by further configuring the control unit 106 to process the temperature profile. For example, in accordance with an exemplary embodiment of the disclosed subject matter, the regression of the temperature over log of time can be performed over an interval of time corresponding to each heat pulse for each sensor location. The slope and intercept of the regression can be used to identify the material characteristics. For example, the regression can take the functional form of $T=b+m \ln(t)$, where T is the temperature measurement, $\ln(t)$ is the natural log of the time of the temperature measurement, b is the intercept of the regression, and m is the regression coefficient.

The interval over which the regression is taken can be, for example, during the heating condition described above (e.g., during which the heat pulse passes over the sensor location). Because heating can occur in a logarithmic manner, taking the regression as a function of the log of time and provide for results with lower error (e.g., a higher correlation coefficient). That is, for example, the temperature as a function of the log of time can be substantially linear over the heating period. Alternatively, the interval over which the regression is taken can be during the cooling condition described above. For purpose of illustration, and not limitation, for a square electrical pulse from 0 current to a constant non-zero value, the constant non-zero current value can correspond to the heating stage, and zero current can correspond to the cooling stage. The slope of the regression for the heating stage can be computed over a fraction of pulse duration when the current is non-zero, while slope of the regression for the cooling stage can be computed over a fraction of the time for which the current changes to zero value. Additionally or alternatively, the regression can take a number of suitable functional forms. For example, an nth order polynomial regression can be taken if the functional form of the temperature profile resembles an nth order polynomial.

Figure 4A:
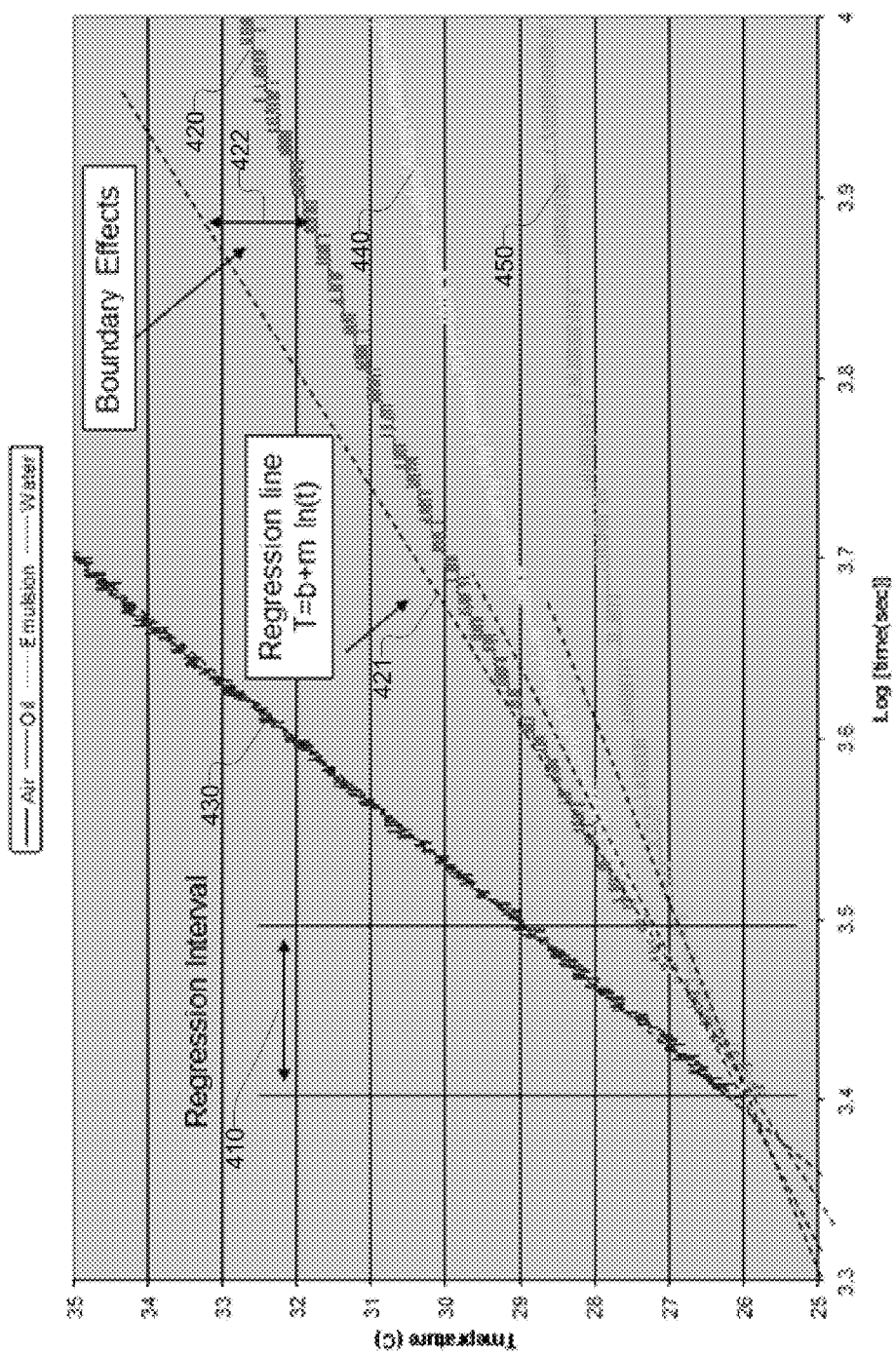
FIG. 4A is a graph illustrating log-time regression sensing technique in accordance with the disclosed subject matter.

For purpose of illustration, FIG. 4A shows the regression results of one temperature measurement at a sensor location in each material of FIG. 3. Line 420 corresponds to a plot of temperature at a sensor location in oil over the log of time. Likewise, lines 430, 440 and 450 correspond to a plot of temperature at a sensor location in air, emulsion, and water, respectively, over the log of time. Regression can be performed over a regression interval 410, which can correspond to the heating condition of the respective temperature sensor. The results of the regression can be plotted. For example, line 421 is a plot of the regression of line 420. As illustrated by FIG. 4A, the slope and intercept of each regression can correspond to a characteristic of the surrounding material, and such characteristics can be determined. That is, with reference to FIG. 4A, each material having different thermal characteristics can have a different slope and intercept, and can thus be identified. As depicted in FIG. 4A, the deviations in measurements resulting from the linear fitting line after the regression interval, as shown by line 420 and line 421, can be due to boundary effects from the wall of the vessel. One of ordinary skill in the art will appreciate that the description of the underlying principles herein assumes the thermal energy delivered by the sensing cable diffuses out without any boundaries. However, in the presence of such boundaries, thermal energy will be contained in a finite space and eventually thermal equilibrium will be reached. Accordingly, the regression interval can be selected based on a desired application, including corresponding boundary conditions.

Figure 4B:
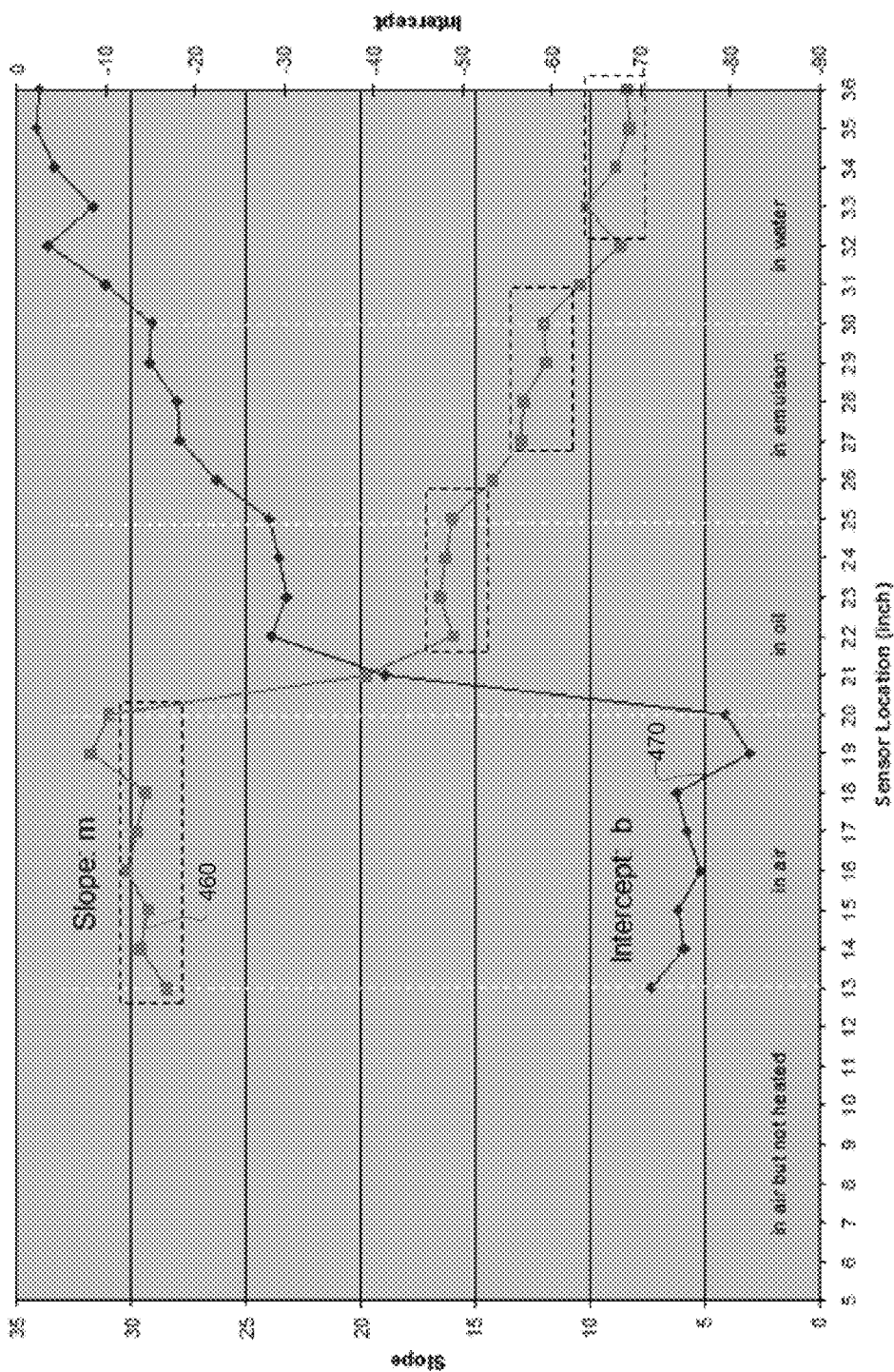
FIG. 4B is a graph illustrating log-time regression sensing technique for a plurality of sensor locations in accordance with the disclosed subject matter.

For purpose of illustration, FIG. 4B shows the regression results for 24 temperature sensors of FIG. 3, showing both slopes 450 and intercepts 470. As illustrated by FIG. 4A and FIG. 4B, in certain circumstances these techniques can provide determination of material characteristics with reduced error, comparing results from FIG. 4B with FIG. 3 to differentiate the emulsion layer and the oil layer. The interval over which the regression can be performed can be predetermined to reduce boundary effect errors (e.g., error 422 induced by boundary effects in the plot of line 420). That is, for example, taking the regression over a small interval can omit certain features of a temperature profile that can correspond to a particular characteristic. Accordingly, the regression interval can be predetermined such that errors induced by boundary effects are reduced. For example, the regression interval can be predetermined by calibration and/or with reference to known parameters or operating conditions of the system, such as expected features of a temperature profile.

In accordance with another aspect of the disclosed subject matter, enhanced determination of the characteristics of media surrounding the sensing cable can be achieved with a control unit 106 configured to process the temperature profile in the frequency domain. A N-pulse train (i.e., application of a certain periodic form of current through the sensing cable to generate N cycles of heating and cooling) can be propagated through the heating/cooling element 103. The period of a heating/cooling cycle, $t_0$, the number of heating cycles, N, and the current amplitude, $I_0$, can be selected. The heating/cooling pulses can be applied to the heating/cooling element 103 with the excitation source 105 to generate thermal excitation within the sensing cable 101.

Temperature readings from the optical fiber sensor array 102 can be collected via the signal interrogator 104 at a selected sampling frequency. The sampling frequency can be, for example, at least twice the maximum signal frequency of interest. A temperature series, $T_i(1)$, $T_i(2)$, $T_i(3)$, . . . can be generated where i=1, 2, 3, . . . M, is the sensor index. In accordance with certain embodiments, synchronized sampling techniques can be employed to reduce the sample number, increase the signal to noise ratio, and improve Fourier transform accuracy. The time difference of the temperature readings $\Delta T=[T(k+1)-T(k)]/\Delta t$, can be calculated using the control unit 106 to generate time series of temperature derivative $\Delta T_i(1)$, $\Delta T_i(2)$, $\Delta T_i(3)$..., where sensor index i=1, 2, 3... M. In connection with the following description, the temperature difference, differenced temperature, or temperature derivatives are all referred to as the time series $\Delta T'$. A transform (e.g., a Fast Fourier Transform [FFT], or Discrete Fourier Transform [DFT]) can be applied, using the control unit 106, to generate a spectrum of time series of temperature difference for M sensors. For each sensor, the real and imaginary values of the spectrum at fundamental frequency of N-Pulse train can be selected $f_0=1/t_0$. The characteristics of the surrounding media can thus be determined as disclosed herein using M pairs of the values derived from the spectrum of the temperature difference as described above. Alternatively, the frequency differenced spectrum (i.e., obtained by applying the operation of taking the derivative of the spectrum of temperature difference with respect to the frequency) and the real imaginary values of the differenced spectrum can be used. The characteristics of the surrounding media can thus be determined as disclosed herein using M pairs of the values derived from the differenced spectrum as described above.

Figure 5A:
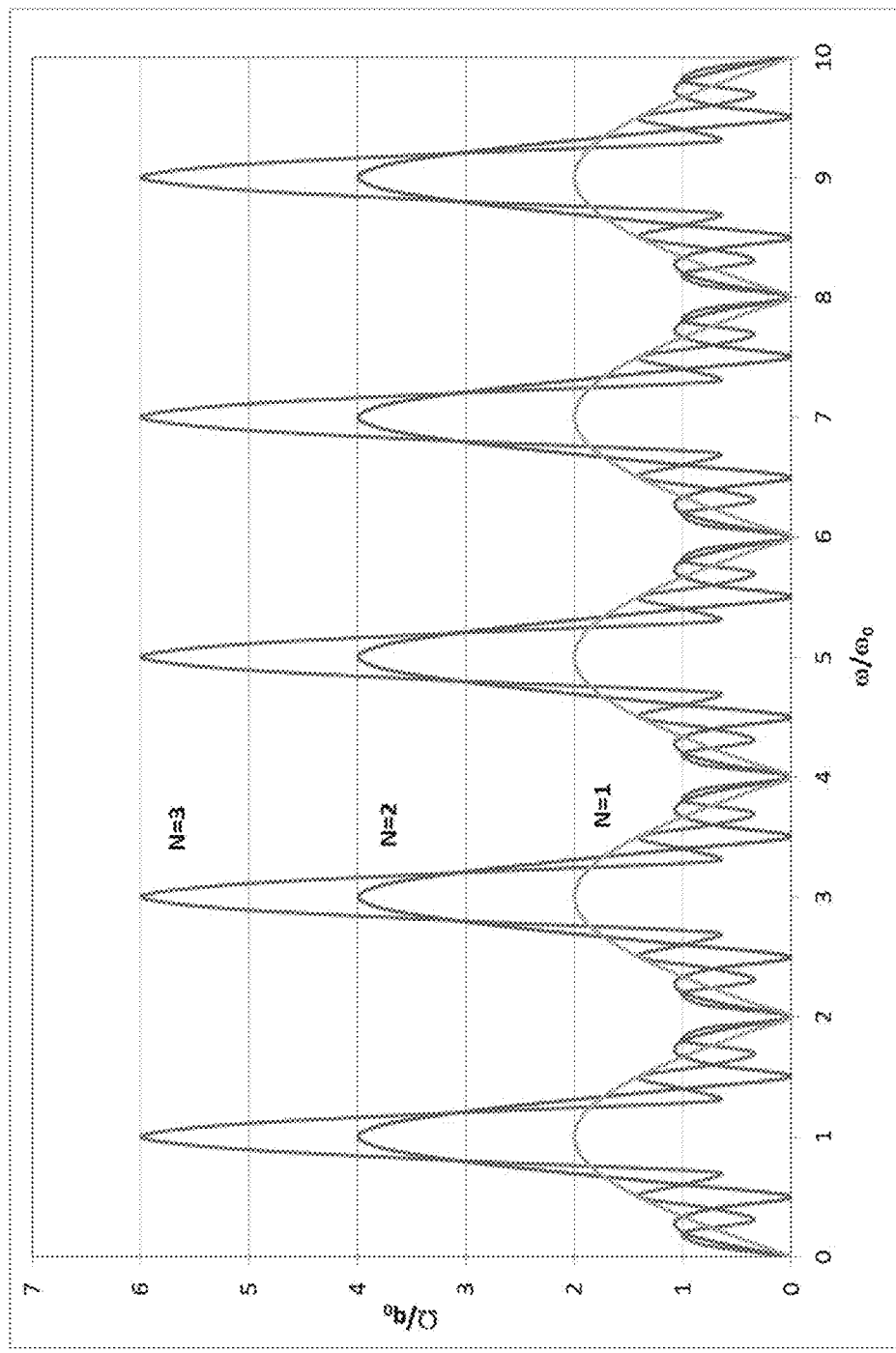
FIG. 5A is a graph illustrating thermal excitation energy concentration at harmonics and fundamental frequencies of heat pulses in connection with a frequency spectrum sensing technique.
Figure 5B:
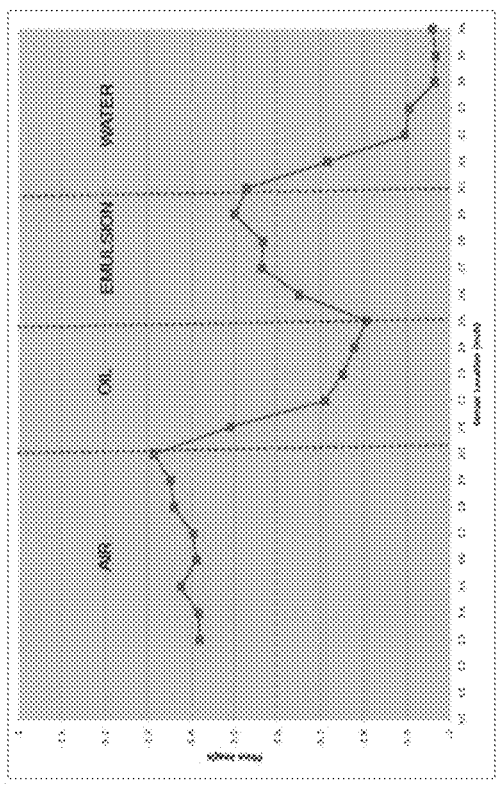
FIG. 5B is a graph illustrating the phase of a frequency-derivative spectrum in connection with frequency spectrum sensing techniques over a plurality of sensor locations in accordance with the disclosed subject matter.
Figure 5C:
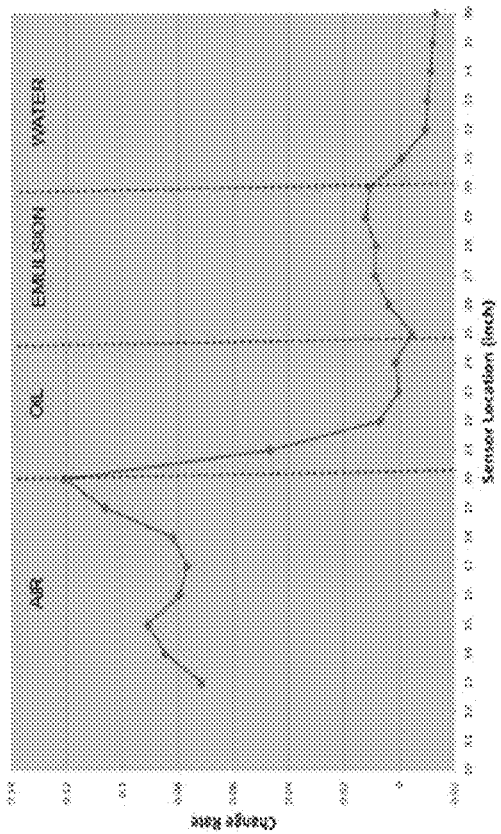
FIG. 5C is a graph illustrating the amplitude of a frequency-derivative spectrum in connection with frequency spectrum sensing techniques over a plurality of sensor locations in accordance with the disclosed subject matter.

That is, for example, the time derivative of the temperature data can be determined (i.e., resulting in the differenced temperature). The Fourier transform of the time-derivative temperature can then be determined, and the derivative of the complex spectrum with respect to the frequency can be calculated (i.e., resulting in the differenced spectrum). The amplitude and phase of the frequency-derivative spectrum (differenced spectrum) can then be calculated. The amplitude and phase of the frequency-derivative spectrum can correspond to the characteristics of the surrounding media at each sensor location. For purpose of illustration, FIG. 5B shows the phase of the frequency-derivative spectrum of the temperature measurements over the sensor locations as illustrated in FIG. 3. Likewise, FIG. 5C shows the amplitude of the frequency-derivative spectrum of the temperature measurements over the sensor locations as illustrated in FIG. 3. As illustrated by the figures, the techniques disclosed herein can provide for enhanced accuracy in the measurement and differentiation of the levels and interfaces between the air, oil, emulsion, and water layers.

As embodied herein, the sensing cable 101 can be calibrated, e.g., with the control unit 106. Calibration can include calibrating the sensor array to ensure that each sensor at a different location along the sensing cable provides the same output when subject to the same material of a constant thermal property. For example, the sensing cable 101 can be submerged into a homogenous medium of known thermal property, and the temperature measurements and processing techniques disclosed herein can be applied. If there is a difference between sensor output, the difference can be used as compensation and can be applied during measurements. Additionally, calibration can include ensuring that the sensor output accurately estimates the particular characteristic of interest (e.g., thermal conductivity and/or diffusivity). For example, a number of materials with known thermal properties can be measured for a broad range of values and a database can be constructed including correlations between measurements and determined characteristics of the known materials. The database can then be used to interpolate a measured characteristic of an unknown material.

Figure 2:
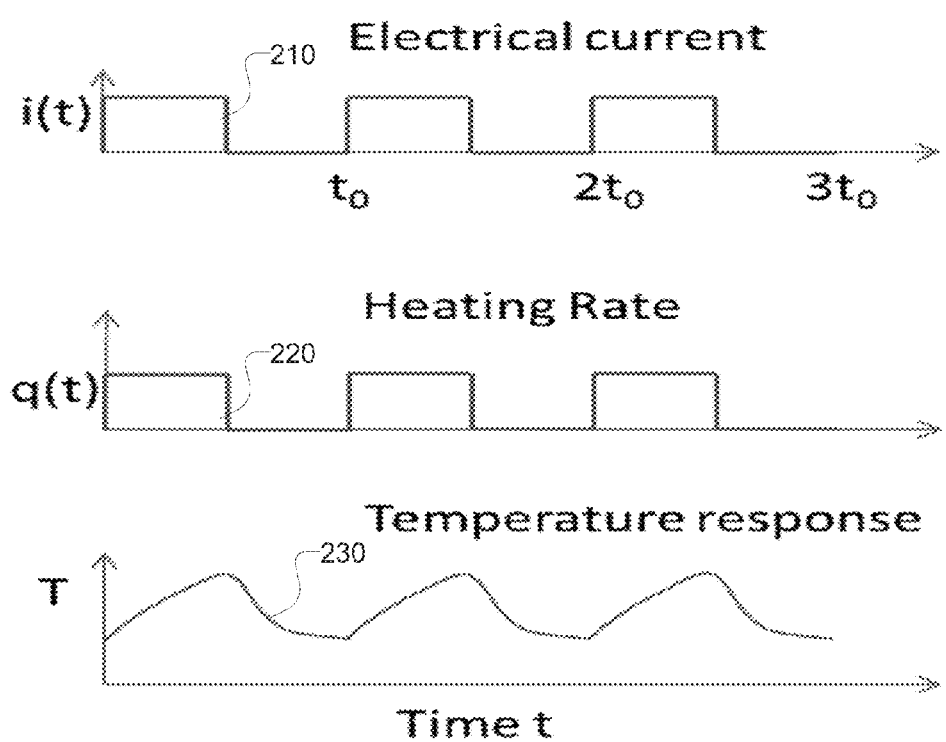
FIG. 2 depicts a representative plot of current and heat pulses and corresponding temperature response in accordance with the disclosed subject matter.

For purpose of illustration, and not limitation, the underlying theory of measurement techniques in accordance with this exemplary embodiment will be described. In connection with this description, for purpose of example, the waveform of the pulse train propagated through the heating device can be a square shape current, e.g., as illustrated in FIG. 2. The current can be defined mathematically as:

$$i(t) = \sum_{n=1}^{N}\left\{H(t-(n-1)t_0) - H\left(t-\left(n-\frac{1}{2}\right)t_0\right)\right\}I_0, \quad (17)$$

where $t_0$ is the period, $I_0$ is the amplitude of the current, and H denotes the Heaviside step function defined by:

$$H(x-x_0) = \begin{cases} 0 & x < x_0 \\ 1 & x \geq x_0 \end{cases}. \quad (18)$$

The heating rate can thus be given as:

$$q(t) = \sum_{n=1}^{N}\left\{H(t-(n-1)t_0) - H\left(t-\left(n-\frac{1}{2}\right)t_0\right)\right\}q_0, \quad (19)$$

where $q_0$ is related to the current by equation 5.

Instead of analyzing the temperature in time domain, the temperature rate, i.e., the derivative of the temperature with respect to time, can be considered in the frequency domain. The derivative operation, a high-pass filtering, can remove the slow-varying trend of the temperature for easier analysis. The time derivative of the temperature and heating generation rate can be defined as follows:

$$\dot{T}(r,t) = \frac{dT}{dt} \quad (20)$$

and $$\dot{q}(t) = \frac{dq}{dt}. \quad (21)$$

In frequency domain, the counterparts to the temperature and heating generation rate can be complex spectrum functions of $S(r, \omega)$ and $\Omega(\omega)$. For large distances away from the heating element, the thermal diffusion process can exhibit the behavior of an attenuated and dispersive wave. The complex spectrum of the change rate of the temperature on the sensing cable's surface can be given as:

$$S(r_0, \omega) = \frac{1}{2\pi k} \frac{\Omega(\omega)}{\kappa r_0} \frac{H_0^{(2)}(\kappa r_0)}{H_1^{(2)}(\kappa r_0)}. \quad (22)$$

The contribution of the heating component, $\Omega$ at a center frequency of $\omega$, to the change rate of the temperature on the sensing cable's surface can thus be given as:

$$d\dot{T}(r_0,\omega,t) = S(r_0,\omega)e^{j\omega t}d\omega. \quad (23)$$

Integration of above over all frequencies can recover the temperature rate in time domain. Therefore, S can be used as indicator of the medium. For purpose of illustration, and not limitation, the excitation term, $\Omega$ will now be described in greater detail. From equations 19 and 21, the derivative of the heating generation can be given as:

$$\dot{q}(t) = \sum_{i=1}^{N} \left\{ \delta(t-(i-1)t_0) - \delta\left(t-\left(i-\frac{1}{2}\right)t_0\right) \right\} q_0 \quad (24)$$

in time domain, and:

$$\Omega(\omega) = q_0 (e^{j\omega t_0} - e^{j\frac{\omega t_0}{2}}) \sum_{n=1}^{N} e^{j(n\omega t_0)} \quad (25)$$

in frequency domain. Because N is finite, $\Omega$ can contain all frequencies. The components at the harmonic frequencies can be given as:

$$\omega_k = k\omega_0 = k\frac{2\pi}{t_0}, \quad (26)$$

with index k.

Evaluation of equation 25 at the harmonic frequencies gives:

$$\Omega(\omega_k) = \begin{cases} 2Nq_0 & k = 1, 3, 5 \ldots \\ 0 & k = 0, 2, 4 \ldots \end{cases} \quad (27)$$

As such, $\Omega$ peaks at odd harmonics but zeros at even harmonics. At non-harmonic frequencies, $\Omega$ is complex in general. FIG. 5A depicts an exemplary plot of $\Omega/q_0$ verse $\omega/\omega_0$ for N=1, 2, or 3. Accordingly, the thermal excitation energy can be concentrated at odd harmonics of fundamental frequency of pulses and increase as N increases.

As embodied herein, one of the odd harmonic frequencies can be chosen to increase signal to noise ratio in analysis of temperature measurements. In this manner, any temperature variation introduced by non-electrical heating can introduce noise which could be difficult to handle in time domain but can be reduced in frequency domain via N-pulse train: the number of cycles, N, can be increased to boost the peak value at odd harmonics. Additionally or alternatively, synchronized sampling techniques or harmonic tracking can also be used to reduce the noise.

In accordance with an exemplary embodiment, the spectrum $S(\omega)$, e.g., as given in equation 22, can be used to estimate the thermal property of a medium surrounding the sensing cable. A characteristic frequency can be given as:

$$\omega^* = \frac{\alpha}{r_0^2}. \quad (28)$$

The complex argument to the Hankel functions can thus become:

$$\kappa r_0 = \sqrt{-j\frac{\omega}{\alpha}} r_0 = \sqrt{\frac{\omega}{\omega^*}} e^{j\theta}, \quad (29)$$

Where $\theta = 3/4\pi$ for $\omega > 0$. At low frequencies where $\omega/\omega^*$ (amplitude of $\kappa r_0$) is less than 1, the Hankel functions can be approximated as:

$$H_0^{(2)}(\kappa r_0) \approx 1 - \frac{(\kappa r_0)^2}{4} - j\frac{2}{\pi}\ln(\kappa r_0) \quad (30)$$

and:

$$H_1^{(2)}(\kappa r_0) \approx \frac{\kappa r_0}{2} - \frac{(\kappa r_0)^3}{16} + j\frac{2}{\pi}\frac{1}{\kappa r_0}. \quad (31)$$

The spectrum, S, can thus reduce to:

$$S(r_0, \omega) = \frac{\Omega}{2\pi k} \hat{X}\left(\frac{\omega}{\omega^*}\right), \quad (32)$$

where the normalized transfer function, and temperature change response to the thermal excitation $\Omega/2\pi k$ at frequency $\omega/\omega^*$ can be given as:

$$\hat{X}\left(\frac{\omega}{\omega^*}\right) = (R_s + jI_s) = X e^{j\phi}, \quad (33)$$

$$R_s \approx \frac{\frac{1}{32}\left(\frac{\omega}{\omega^*}\right)^2 + \frac{1}{2\pi}\frac{\omega}{\omega^*} + \frac{1}{2\pi}\left(\frac{\omega}{\omega^*} - \frac{4}{\pi}\right)\ln\left(\frac{\omega}{\omega^*}\right)}{\frac{1}{4}\left(\frac{\omega}{\omega^*}\right)^2 - \frac{2}{\pi}\left(\frac{\omega}{\omega^*}\right) + \frac{4}{\pi^2}}, \quad (34)$$

and $$I_s \approx \frac{\frac{5}{4}\left(\frac{\omega}{\omega^*} - \frac{4}{\pi}\right) - \frac{1}{16\pi}\left(\frac{\omega}{\omega^*}\right)^2 \ln\left(\frac{\omega}{\omega^*}\right)}{\frac{1}{4}\left(\frac{\omega}{\omega^*}\right)^2 - \frac{2}{\pi}\left(\frac{\omega}{\omega^*}\right) + \frac{4}{\pi^2}}, \quad (35)$$

after neglecting terms of higher order.

As disclosed herein, and in accordance with an exemplary embodiment of the disclosed subject matter, the amplitude and phase can decrease monotonically with frequency so that higher frequency corresponds with lower response of temperature to the heating. Accordingly, lower frequencies can obtain significant heating response and higher signals. Additionally, the imaginary part of the complex spectrum can be nearly linear with the frequency while the real part can exhibit linear behavior beyond certain frequency values. Therefore, the derivative of the transfer function spectrum with respect to frequency can lead to constants beyond certain values of $\omega/\omega^*$. One of ordinary skill in the art will appreciate that, mathematically, the spectral derivative is equivalent to the Fourier transform of the temperature rate with respect to the log of time. Thus there is connection of the derivative spectrum with the linear relationship of the temperature change with $\log(t)$ in the time domain as shown in equation 13.

As embodied herein, systems and methods in accordance with the disclosed subject matter include determining the liquid/gas flow distribution of a fluid through a component with a sensing cable including an optical fiber sensor array aligned with a heating/cooling element. The method includes propagating at least one heating/cooling pulse through the heating/cooling element along at least a portion of the sensing cable to affect an exchange of thermal energy between the heating element and the fluid exposed to the sensing cable. The method includes measuring, over time, a temperature profile of the sensing cable corresponding to the heat pulse at each of a plurality of sensor locations on an optical fiber sensor array. The method includes determining a flow distribution of the fluid by determining one or more properties of the fluid exposed to the sensing cable at each of the plurality of sensor locations based on the temperature profile corresponding thereto.

For purpose of illustration and not limitation, reference is made to the exemplary embodiments of FIG. 1. The method and system disclosed herein can be used to determine flow distribution in variety of components and vessels. For example, the component can be a particulate bed (such as a catalyst bed), a wash bed including a packing material, an absorbent bed, a structured bed, a filter, or the like. In operation, it can be desirable to determine flow conditions through such components. For example, fixed bed reactors, such as hydrotreating reactors and hydrocracking reactors, can develop liquid/gas maldistribution and corresponding localized "hot spots" in their respective catalyst bed(s), which can cause a runaway condition in exothermic reactions within the reactor. As another example, liquid/gas maldistribution can occur in components such as the wash beds of a vacuum pipe still ("VPS") distillation tower, which can cause problems such as unplanned capacity loss, increased operational costs, and increased energy usage. Determination of flow distribution of a fluid through such components can allow for mitigation strategies, such as increasing the flow rate of wash oil or otherwise varying operational parameters of the component. Accordingly, the techniques disclosed herein can be employed to determine the flow distribution of a fluid through a component in connection with a refining operation. However, it is recognized that the system and method herein can be applied to numerous other environments and vessels in which the determination of flow distribution is beneficial.

Figure 1B:
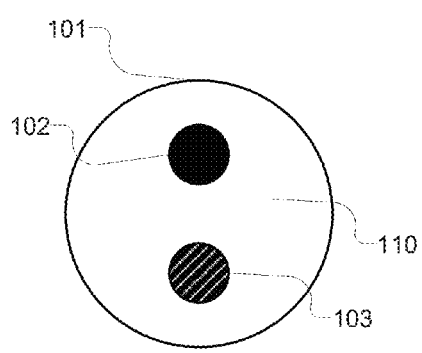
FIG. 1B is a cross sectional view of an exemplary sensing cable configuration in accordance with the disclosed subject matter.
Figure 1C:
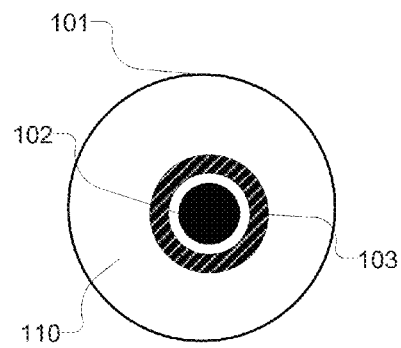
FIG. 1C is a cross sectional view of another exemplary sensing cable configuration in accordance with the disclosed subject matter.

In accordance with this exemplary embodiment, the system for detecting a liquid/gas flow distribution vessel can include the components and features described herein with reference to FIG. 1A-C. The sensing cable (e.g., sensing cable 101) can further include an anti-fouling coating to resist fouling and/or coking deposition on the sensing cable. For example, the sensing cable can be coated with a suitable coating to resist coking, such as Teflon, or coatings formed from modified fluoropolymer and co-polymer reinforcements. These coatings can be engineered for high release (non-stick), non-wetting, thermal stability, dielectric strength and chemical resistance, where comparatively thin films are desired or otherwise beneficial.

Using the systems and techniques as disclosed, and suitable modifications as desired, a method of determining the flow distribution of a fluid through a component is provided and disclosed herein with reference to FIG. 1A through FIG. 5. For purpose of example, and with reference to FIG. 6, the method of determining the flow distribution of a fluid through a component will be described in connection with certain exemplary embodiments, wherein the vessel is a fixed catalyst (i.e., particulate) bed, such as in a fixed catalyst bed of a hydrotreating or hydrocracking reactor or a fixed wash oil (i.e., structured or packed) bed of a VPS distillation tower.

In an embodiment, the component is a hydroprocessing reactor (i.e., a reactor vessel for catalytically reacting a hydrocarbon in the presence of a catalyst and hydrogen) which includes a particulate bed, and the particulate bed is comprised of catalyst particles. In a preferred embodiment, such catalyst particles are comprised of a hydrodesulfurization catalyst (i.e., a catalyst effective for removing sulfur atoms/compounds from hydrocarbons), a hydrodenitrogenation catalyst (i.e., a catalyst effective for removing nitrogen atoms/compounds from hydrocarbons), a hydrodeoxygenation catalyst (i.e., a catalyst effective for removing oxygen atoms/compounds from hydrocarbons), a hydrocracking catalyst (i.e., a catalyst effective for cracking hydrocarbons into lower molecular weight compounds), a hydroreforming catalyst (i.e., a catalyst effective for producing aromatic hydrocarbon compounds by reforming non-aromatic hydrocarbons), a hydroisomerization catalyst (i.e., a catalyst effective for producing iso-paraffinic compounds from non-iso-paraffinic hydrocarbons), or any combination thereof. One of ordinary skill in the art will appreciate that the techniques disclosed herein can be applied in connection with a variety of suitable components, and the disclosed subject matter is not intended to be limited to the exemplary embodiments disclosed herein.

Figure 6:
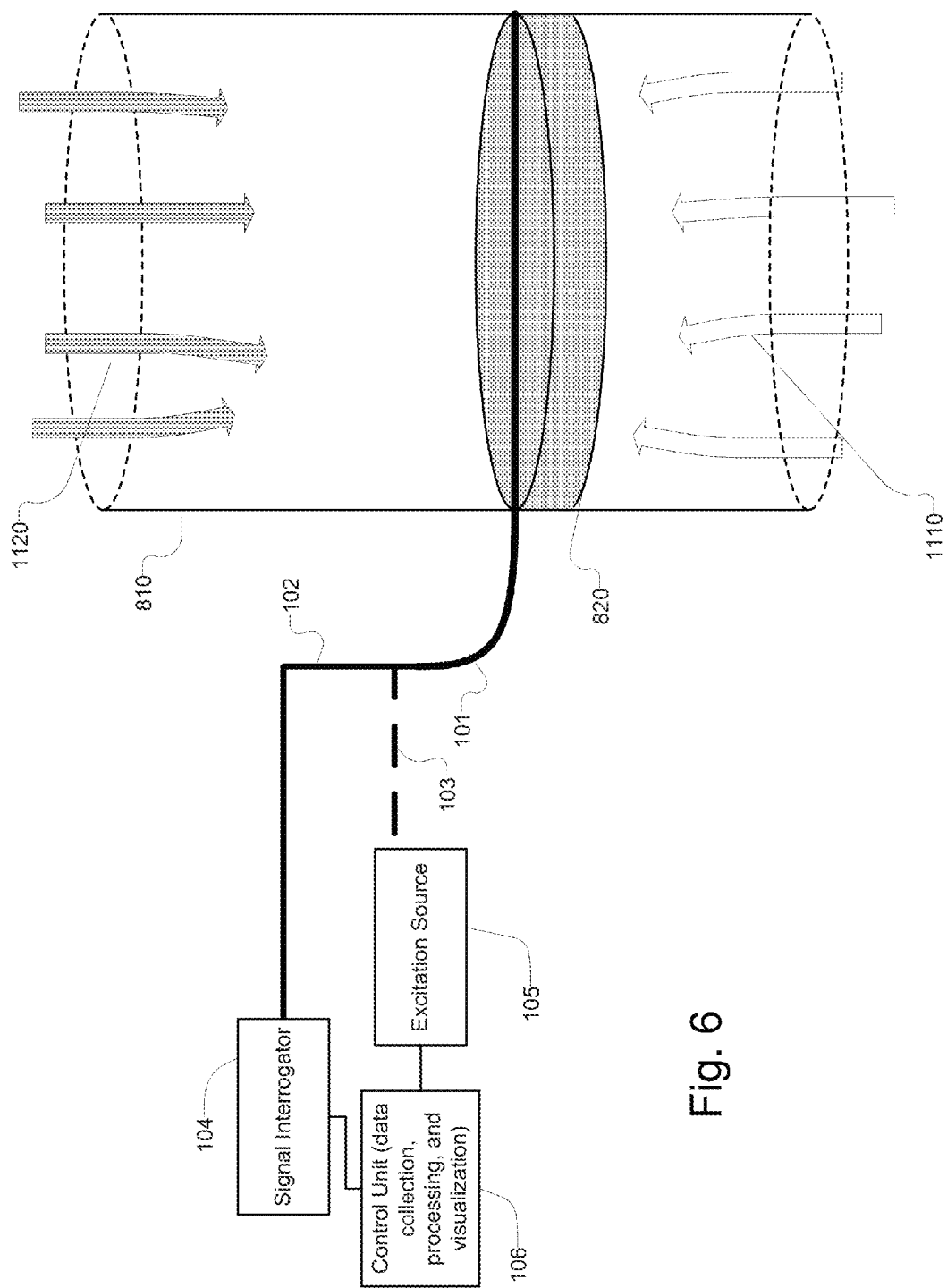
FIG. 6 is a schematic representation of a system for determining flow distribution through a component in accordance with an exemplary embodiment of the disclosed subject matter.
Figure 8:
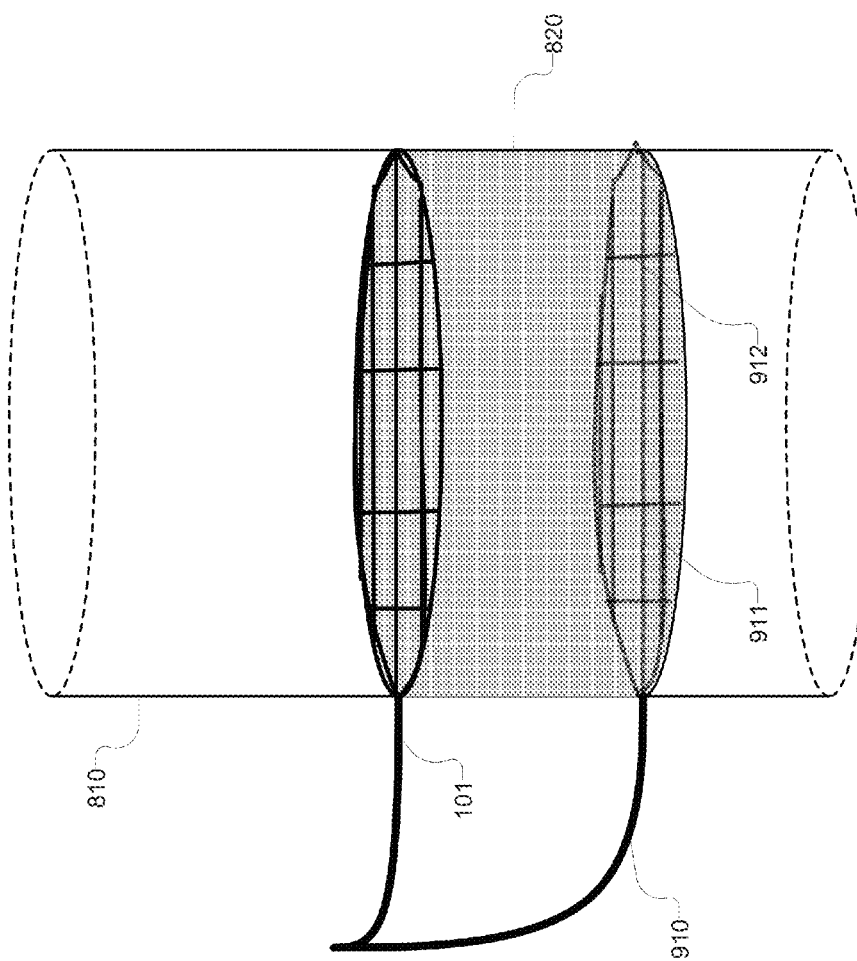
FIG. 8 is a schematic representation of a plurality of sensing cables arranged in grid patterns in accordance with an exemplary embodiment of the disclosed subject matter.

With reference to FIG. 6, the method of flow through a vessel 810 can include positioning a sensing cable 101 within a wash bed 820 of a VPS distillation tower 810. For example, the sensing cable 101 can be positioned across a surface of the wash bed 820 such that the sensing cable 101 is aligned perpendicular to an axis of the vessel 810. In this manner, sensor locations along the sensing cable 101 can correspond to locations about a cross section of the vessel 810. The sensing cable 101 likewise can be positioned and/or arranged in a variety of other suitable configurations as desired or needed. For example, the sensing cable 101 can be positioned parallel to an axis of the vessel 810 with the sensor locations along the sensing cable 101 generally correspond to locations along a vertical axis within the vessel 810, such as along an inside wall of the vessel 810. Moreover, as shown in FIG. 8, the sensing cable 101 can be arranged in a grid pattern or array 911 and 912, or any other suitable pattern, about a surface of the wash bed 820 or otherwise within the vessel 810. One of ordinary skill in the art will also appreciate that more than one sensing cable can be employed. For example, as depicted in FIG. 8, a second sensing cable 910, which can also be positioned in a grid pattern, can be positioned on an opposite surface of the wash bed 820.

As previously noted, the sensing cable 101 includes a heating/cooling element 103, such as a heating wire, and an optical fiber sensor array 102, as disclosed herein. The optical fiber includes a plurality of sensing locations along the length of the fiber, such that each sensing location corresponds to a position about the surface of the wash bed 820. For example, and as previously noted, the optical fiber can include a plurality of sensors along its length and/or a single fiber sensor can be movable to define a plurality of sensor locations. The optical fiber sensor is coupled to an optical signal interrogator 104 to process an optical signal therein to obtain temperature measurements at each of the sensor locations. The optical signal interrogator 104 can further be coupled to a control unit 106 to process the temperature measurements.

As previously described herein, the heating wire is coupled to an excitation source 105 adapted to propagate electromagnetic waves (e.g., current 210) through the heating wire, thereby creating corresponding heat pulses (e.g., heat pulse 220). As the heat pulses propagate through the heating wire, heat is exchanged between the heating wire, the sensing cable, and the surrounding media at each sensor location. The temperature at each sensor location can be recorded, e.g., via the optical signal interrogator and control unit, to generate a temperature profile for each sensor location. For example, temperature can be measured as a function of time at each sensor location along the optical fiber. The temperature profile at each sensor location generally will correspond to the characteristics of the medium surrounding the sensing cable at that sensor location. In this manner, for purpose of illustration, sensor locations over which fluid in the vessel 810 is flowing can result in a temperature profiles distinguishable from sensor locations over which fluid is not flowing.

The temperature profile (i.e., the temperature as a function of time at a sensor location) can generally exhibit an increase in temperature coinciding with the exposure to the heat pulse at the corresponding sensor location. For purpose of illustration, and not limitation, and with reference to the laws of thermodynamics, the temperature will generally increase over the duration of the heat pulse at a rate corresponding to the characteristics of the surrounding media, and thereafter decrease as the heat from the heat pulse diffuses into the surrounding media at a rate corresponding to the characteristics of the surrounding media. Thus, the temperature profiles for each sensor location can correspond to the characteristics of the surrounding media, e.g., the rate of flow of the surrounding media. For example, and not limitation, at a sensing location over which the surrounding fluid has a substantial flow, the heat transfer from the heating wire into the surrounding media can be relatively high due to convective heat transfer arising from the flow, and thus a cold spot/region can be detected. By contrast, at a sensing location exposed to stationary media, the heat transfer from the heating wire into the surrounding media can be relatively low due to the lack of convective heat transfer, and thus a hot spot/region can be detected. That is, for purpose of illustration, and with reference to Equation 1 and Equation 3, heat loss at a particular sensor location can depend on the rate of flow of the fluid surrounding that sensor location due to convective heat transfer from the sensing cable into the surrounding fluid. Additionally, assuming a homogenous medium of constant temperature flowing within the component, the flow rate of the medium can be determined at each sensor location. Moreover, assuming a medium having a non-uniform temperature and substantially constant flow across the sensing cable, the temperature of the medium without heating pulse can be measured first, follow by measurement of the temperature of the medium with heating pulse. The difference between the temperature measurement without the heating pulse and the temperature measurements with the heating pulse can indicate the flow rate of the medium.

Figure 7:
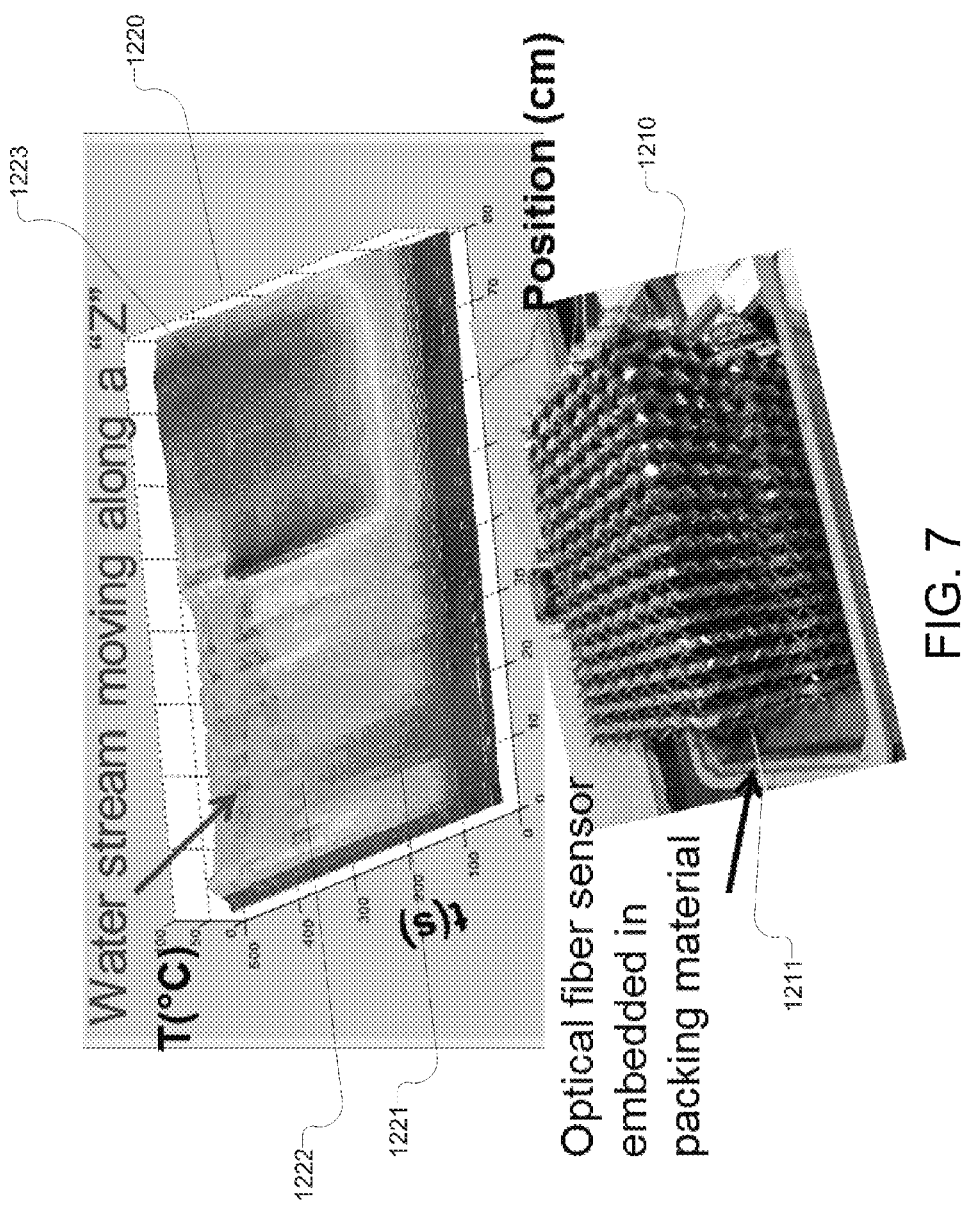
FIG. 7 is an image and graph illustrating an exemplary system and method for determining flow distribution through a component in accordance with the disclosed subject matter.

For purpose of illustration, and not limitation, reference will be made to an example of the method disclosed herein with reference to FIG. 7. FIG. 7 includes an image 1210 of a sensing cable 1211 embedded between two layers of packing material. The sensing cable 1211 can include an optical fiber sensor array adjacent a heating wire. A water stream can be arranged to flow through a portion of the packing material (e.g., from the top layer, over the sensing cable 1211, and through the bottom layer). As depicted in the image 1210 of FIG. 7, the water stream is initially directed through the packing material at a location approximately corresponding to 10-20 cm along the sensing cable 1211. As a heat pulse propagates through the heating wire, heat is exchanged between the heating wire, the sensing cable 1211, the surrounding packing material, air, and the water stream flowing over the sensing cable 1211. During heating, overall temperature readings at each sensor location increase, and the temperature profile reveals the location of the water stream. For example, FIG. 7 includes a plot 1220 of temperature (z-axis) versus sensor location in meters (x-axis) as a function of time (y-axis). Plot 1220 shows a trough of cooler temperature profiles corresponding to the water stream due to convective heat loss. The region 1223 of plot 1220 corresponds to the sensor locations along the sensing cable 1221 exposed to air and outside packing material, and illustrates a relatively higher temperature profile due to lack of convective heat loss. As depicted in FIG. 7, at approximately 400 seconds, the water stream was moved back and forth about the sensing cable 1211. As illustrated by plot 1220, wherever the water flow passes over the sensing cable 1221, the temperature profiles at corresponding sensor locations 1222 will be lower. The "Z" pattern represents a cold temperature region can is caused by the water stream moving back and forth.

As disclosed herein, the control unit thus can be adapted to determine the characteristics of the surrounding media at each sensor location using a variety of techniques, and thereby determine the flow distribution of a fluid through a component. For example, referring again to FIG. 6, the control unit 106 can be adapted to determine, with reference to the known positions of the sensor locations and the corresponding temperature profiles, a relative rate of flow at each sensor location and thus determine the flow distribution of the media surrounding the sensing cable. In connection with the operation of a VPS distillation tower 810, for example, vapor 1110 can flow upwards through one or more wash beds 820 such that different fractions (i.e., different petrochemicals in the vapor) can be separated. However, during operation, coking can occur on the wash bed, which can create uneven flow of vapor 1110 through the tower 810. Accordingly, the methods disclosed herein can determine the flow distribution of the vapor 1110 and thus detect a maldistribution condition associated with coking. VGO wash oil 1120 can be introduced into the VPS distillation tower 810 to prevent the formation of coke deposits, for example upon detection of a coking condition. The methods disclosed herein can likewise determine the flow rate and distribution of the wash oil 1120.

For purpose of illustration, and not limitation, the direct temperature measurement techniques described above can be used to determine the flow distribution of a fluid through a component. Particularly, a feature temperature profile (e.g., including three temperature measurements corresponding to a heating period, a peak temperature measurement, and a cooling period) can be extracted and processed to determine characteristics of the medium surrounding each sensor location. For example, and as depicted in FIG. 7, the temperature profile of sensors exposed to a medium having a flow characteristic can have a relative low peak, heating, and cooling temperature relative to the temperature profile of sensors exposed to a stationary medium of the same kind.

Alternatively, and as described herein with reference to FIG. 4B, a log-time regression technique can be used to determine certain characteristics of the medium surrounding each sensor location by further processing the temperature profile at each sensor location. That is, by performing the regression of the temperature over log of time over an interval of time corresponding to each heat pulse for each sensor location, the resulting slope and intercept of the regression can be used to identify characteristics of the medium. For example, the slope and intercept of sensor locations exposed to a medium having a flow characteristic can be distinguishable from the slope and intercept of sensor locations exposed to the same medium having a stationary characteristic.

In accordance with another exemplary embodiment of the disclosed subject matter, the frequency spectrum techniques disclosed herein with reference to FIG. 5A-C can be employed to determine the flow distribution of a fluid through a component with increased measurement sensitivity, accuracy, and/or reliability. In this exemplary embodiment, and as described above, an N-pulse train can be propagated through the heating wire of the sensing cable 101 with pre-selected parameters, including heating cycle period, $t_0$, number of heating cycles, N, and current amplitude, $I_0$. The parameters can be selected according to the operating characteristics of the component such that the resulting temperature profile can be measured with a desired signal-to-noise ratio. For example, a longer heating cycle period or higher current amplitude can result in higher signal-to-noise ratio relative to a shorter heating cycle period or lower current amplitude. Likewise, an increase in the number of heating cycles can further increase the signal-to-noise ratio. One of ordinary skill in the art will appreciate that such parameters can be varied depending upon desired application. For example, if determination of flow distribution is desired at short time intervals, a shorter heating cycler period and a higher current amplitude can be employed. For purpose of example, and not limitation, in connection with a fixed bed reactor or VPS distillation tower having a diameter of approximately 20 to approximately 40 feet, approximately 4 to 5 layers of wash bed packing materials, and a total height of approximately 6 to approximately 10 feet. The heating cycle period for the sensing cable can be approximately 1 Hz or slower (i.e., the excitation source can be adapted to deliver a current pulse at 1 Hz or slower. The current amplitude can be several mili-amperes to several amperes. One of ordinary skill in the art will appreciate that, in accordance with the disclosed subject matter, suitable frequency and current amplitude can be determined for a particular application by routine testing in accordance with known methods.

The optical signal interrogator 104 can be adapted to measure temperatures from the optical fiber at a pre-selected sampling frequency. In accordance with an exemplary embodiment, the sampling frequency can be at least twice the expected frequency of the temperature profile and/or heat pulse. For example, and not limitation, in connection with a fixed bed reactor or VPS distillation tower, the sampling frequency can be 10 Hz. The derivative with respect to time of the temperature measurements for each sensor location can then be generated. For example, the measured temperatures a sensor location at each sampling interval can be given as a temperature series. The difference between each temperature in the series can then be calculated to generate a temperature derivative series. A transform (e.g., a FFT or DFT) can be applied to convert the temperature derivative series into the frequency domain, and thus generate a spectrum of time series of temperature differences for each sensor location. The derivative of the spectrum, with respect to the frequency, can be generated. That amplitude and phase of the frequency-derivative spectrum (e.g., the real and imaginary parts of the complex frequency-derivative spectrum) can then be determined. For example, using the heating cycle period, $t_0$, the real and imaginary values of the spectrum at the fundamental frequency of the N-pulse train can be selected at $f_0=1/t_0$.

The amplitude and phase of the frequency-derivative spectrum at each sensor location thus can correspond to the characteristics of the medium surrounding the sensing cable 101 at a particular sensor location. For example, the amplitude and phase can decrease monotonically with frequency so that higher frequency corresponds with lower response to a change in temperature from the heating element. Accordingly, lower frequencies can obtain significant heating response and higher signals. Additionally, the imaginary part of the complex spectrum can be nearly linear with the frequency while the real part can exhibit linear behavior beyond certain frequency values. Therefore, the derivative of the transfer function spectrum with respect to frequency can correspond to the linear relationship of the temperature change with log(t) in the time domain. In this manner, the amplitude and phase of sensor locations exposed to a flowing medium can be distinguishable from the amplitude and phase of sensor locations exposed to non-flowing medium of the same kind, or a higher-velocity flowing medium from a lower-velocity flowing medium.

The sensing cable 101 can be calibrated, e.g., with the control unit. Calibration can include, for example, calibrating the sensor array to determine the amplitude and phase of the frequency-derivative spectrum of certain known media. For example, a number of materials with known thermal properties can be measured for a broad range of values and for a broad range of flow rates, and a database can be constructed including correlations between the generated amplitude and phase and characteristics, such as flow rate, of the known materials. The database can then be used as to determine the flow rate of the surrounding medium at a particular sensor location in the vessel.

The control unit 106, with reference to the known locations of each sensor and the corresponding amplitude and phase of the frequency-derivative spectrum, can determine the flow distribution of a fluid through the component. To determine the flow distribution, the control unit can be configured to store the known position of each sensor location in one or more memories. For example, for a 36 inch long sensing cable, having 36 sensor locations each spaced apart by a unit inch, positioned about the surface of a 36 inch wash bed 820, the control unit can store the distance of each sensor location from the wall of the component 810 (i.e., for sensor location $i=\{1, 2, \ldots, 36\}$, the control unit can store a corresponding distance measurement $D_i=\{1 \text{ in}, 2 \text{ in}, \ldots, 36 \text{ in}\}$). For each sensor location, i, the control unit can determine the amplitude and phase of the frequency derivative spectrum as disclosed herein. With reference to, for example, a database storing the amplitude and phase of the frequency derivative spectrum for known flow rates of the known media, the control unit can thus determine the relative flow rate at each sensor location and thus the flow distribution using the determined amplitude and phase at each sensor location.

Additionally or alternatively, and as embodied herein, the control unit can process the determined amplitude or phase of the frequency derivative spectrum of adjacent sensor locations to determine the flow distribution. That is, for example, assuming the vessel contains media with otherwise constant characteristics, a change in the amplitude across two sensor locations can correspond to a different flow rate across the two sensor location. Likewise, a change in the phase can correspond to a different flow rate of the same media. In certain embodiments, the control unit can process both the amplitude and phase of adjacent sensors to enhance determination of flow distribution. For example, a change in both the amplitude and phase can correspond a different flow rate across the two sensors. Moreover, in certain embodiments, the control unit can monitor the amplitude and phase of each sensor location over time (e.g., throughout the operation of a VPS distillation tower) and determine whether the temperature profile of one or more sensor locations changes with time. For example, the control unit can be configured to monitor the temperature profile of one or more sensor locations over time, identify a change in said temperature profile and, with reference, e.g., to a database of known characteristics corresponding to flow rate, determine the flow distribution.

In another exemplary embodiment, multiple layers of sensors can be deployed between different layers of packing materials, for example as depicted in FIG. 8. Measurement from each layer of sensor can reveal localized conditions, such as the flow rate at each sensor location. In this manner, entrainment of resid can be inferred by comparison of measurement results across sensor layers.

The techniques disclosed herein can provide for continuous determination of flow distribution through a component. No moving mechanical parts need be included inside the sensing cable. Because material thermal properties can be measured for determination of flow distribution, the measurement results can be independent of electrical conductivity, salinity, and crude oil constituents, such as sulfur, iron sulfide/oxide. Moreover, relative temperature changes before and after heating/cooling can be used to infer material thermal properties for determination of flow distribution, and temperature baseline can be taken each time before heating/cooling is applied. Accordingly, the methods disclosed herein need not require long term stability for temperature sensors.

Moreover, the system disclosed herein can operate at temperatures ranging from cryogenic temperatures up to over 1000° C. The size of the sensing cable can be relatively small (e.g., compared to conventional thermocouples) and can be cost effective for large area coverage with a large amount of sensors. Utilizing cost-effective optical fiber temperature sensors, the system disclosed herein can incorporate a large number of sensors, and can offer a high spatial resolution, e.g., less than 1 mm, over a long measurement range, e.g., several meters to kilometers. The diameter of the compact sensing cable can small, e.g., less than 2 mm. The small diameter of the sensing cable can allow for measurement in a tight space with reduced intrusiveness. Furthermore, the heating/cooling element can be turned off, and the sensing cable can be converted to a temperature sensor, which can provide absolute temperature measurements inside the vessel, such as measurements of the wash bed packing materials. Such absolute temperature measurements can be used to infer liquid/vapor distributions, for example, inside packing materials, where temperature differences between liquid and vapor.

ADDITIONAL EMBODIMENTS

Additionally or alternatively, the invention can include one or more of the following embodiments.

Embodiment 1

A method for determining the flow distribution of a fluid through a component, comprising: providing within a component a sensing cable including an optical fiber sensor array aligned with a heating element; propagating at least one heat pulse through the heating element along at least a portion of the sensing cable to affect an exchange of thermal energy between the heating element and the fluid exposed to the sensing cable; measuring, over time, a temperature profile of the sensing cable corresponding to the heat pulse at each of a plurality of sensor locations on the optical fiber sensor array; and determining a flow of the fluid by determining one or more properties of the fluid exposed to the sensing cable at each of the plurality of sensor locations based on the temperature profile corresponding thereto.

Embodiment 2 the method of any one of the previous embodiments, wherein the component includes a particulate bed, a wash bed including packing material, an absorbent bed, a structured bed, or a filter. In a further embodiment thereof, the component is a hydroprocessing reactor which includes a particulate bed and the particulate bed is comprised of catalyst particles. In yet a further embodiment thereof, the catalyst particles are comprised of a hydrodesulfurization catalyst, a hydrodenitrogenation catalyst, a hydrodeoxygenation catalyst, a hydrocracking catalyst, a hydroreforming catalyst, a hydroisomerization catalyst, or any combination thereof.

Embodiment 3 the method of any one of the previous embodiments, wherein measuring, over time, the temperature profile includes measuring using fiber Bragg grating array based sensing, Raman scattering based sensing, Rayleigh scattering based sensing, or Brillioun scattering based sensing.

Embodiment 4 the method of any one of the previous embodiments, wherein the heating element includes a resistive heating element and wherein propagating the at least one heat pulse includes applying an electrical pulse with a predetermined frequency and predetermined waveform.

Embodiment 5 the method of any one of the previous embodiments, wherein propagating at least one heat pulse through the heating element includes propagating the at least one heat pulse through a heating element aligned adjacent to the optical fiber sensor array.

Embodiment 6 the method of embodiments 1, 2, 3, or 4, wherein propagating at least one heat pulse through the heating element includes propagating the at least one heat pulse through a heating element disposed concentrically with the optical fiber sensor array.

Embodiment 7 the method of embodiments 1, 2, 3, 5 or 6, wherein the heating element includes a thermoelectric device and wherein propagating at least one heat pulse through the heating element includes propagating cooling pulse.

Embodiment 8 the method of any one of the previous embodiments, further comprising coating the sensing cable with an antifouling coating to prevent formation of deposits thereon.

Embodiment 9 the method of any one of the previous embodiments, wherein the sensing cable further includes an outer diameter including a metal and mineral insulation material.

Embodiment 10 the method of any one of the previous embodiments, wherein measuring the temperature profile corresponding to the heat pulse at each of the plurality of sensor locations includes, for each sensor location, measuring at least a heating temperature measurement during propagation of the heat pulse over the sensor location, a peak temperature measurement, and a cooling temperature measurement after propagation of the heat pulse over the sensor.

Embodiment 11 the method of any one of the previous embodiments, wherein measuring the temperature profile corresponding to the heat pulse at each of the plurality of sensor locations includes, for each sensor location, measuring a plurality of temperatures over a period of time upon arrival of the heat pulse at the sensor location.

Embodiment 12 the method of embodiment 11, wherein determining the flow of the fluid includes, for each temperature profile, performing a regression of the plurality of temperatures over a logarithm of corresponding measurement times for a predetermined time window in the period of time to generate a slope and an intercept of the regression, wherein the slope and the intercept relate to the flow of the fluid over the sensing cable at the sensor location.

Embodiment 13

The method of claim 12, wherein the predetermined time window includes a time window during a heating stage, the heating stage corresponding to a period of time during propagation of the heat pulse over the sensor location or a time window during a cooling stage, the cooling stage corresponding to a period of time after propagation of the heat pulse over the sensor.

Embodiment 14 the method of embodiment 11, 12 or 13, wherein determining the flow of the fluid includes, for each temperature profile: generating a time derivative by calculating a derivative of the plurality of temperature measurements with respect to time; applying a transform to the time derivative to generate a complex spectrum; and determining an amplitude and a phase of the complex spectrum, wherein the amplitude and the phase of the complex spectrum relate to the flow of the fluid over the sensing cable at the sensor location.

Embodiment 15

The method of claim 14, wherein determining the flow of the fluid further includes, for each temperature profile: generating a frequency derivative spectrum by calculating the derivative of the complex spectrum with respect to frequency; and determining an amplitude and a phase of the frequency derivative spectrum, wherein the amplitude and the phase of the frequency derivative spectrum relate to the flow of the fluid over the sensing cable at the sensor location.

Embodiment 16 the method of any one of the previous embodiments, wherein determining the flow of the fluid further includes detecting a misdistribution condition in the component by monitoring the temperature profile corresponding to each of the plurality of sensor locations, and comparing the monitored temperature profiles to predetermined temperature profiles corresponding to a desired operation condition.

Embodiment 17 the method of any one of the previous embodiments, wherein determining the flow of the fluid further includes detecting a misdistribution condition in the component by monitoring a first temperature profile corresponding to each of the plurality of sensor locations and at least a second temperature profile corresponding to each of the plurality of sensor locations, and comparing the first and second temperature profiles to detect a change in operation condition.

Embodiment 18 the method of any one of the previous embodiments, wherein the sensing cable is disposed in a grid configuration within the component, further comprising generating a multi-dimensional flow distribution based on the temperature profile corresponding to each sensor location.

Embodiment 19 the method of any one of the previous embodiments, wherein the sensing cable further includes a plurality of sensing cables, wherein each of the plurality of sensing cables is disposed within different layers of the component, and wherein the control unit is further configured to generate a multi-dimensional flow distribution based on the temperature profile corresponding to each sensor location.

Embodiment 20 the method of any one of the previous embodiments, wherein the component has an operating temperature between cryogenic temperatures and approximately 1000° C., wherein the sensing cable has a diameter of less than 2 mm, and wherein the optical signal interrogator is configured to measure the temperature profile at a spatial resolution less than 1 mm.

Embodiment 21

A system for determining the flow distribution of a fluid through a component, comprising: a sensing cable including an optical fiber sensor array aligned with a heating element disposed in the component, the optical fiber sensor array having a plurality of sensor locations; an excitation source coupled with the heating element and configured to propagate at least one heat pulse through the heating element along at least a portion of the sensing cable to affect an exchange of thermal energy between the heating element and the fluid exposed to the sensing cable; an optical signal interrogator coupled with the optical fiber sensor array and adapted to receive a signal from each of the plurality of sensor locations and configured to measure, over time, a temperature profile of the sensing cable corresponding to the heat pulse at each of the plurality of sensor locations on the optical fiber sensor array; and a control unit, coupled with the heating element and the optical signal interrogator, to determine a flow of the fluid by determining one or more properties of the fluid exposed to the sensing cable at each of the plurality of sensor locations based on the temperature profile corresponding thereto.

Embodiment 22 the system of embodiment 21, wherein the component includes a particulate bed, a wash bed including packing material, an absorbent bed, a structured bed, or a filter. In a further embodiment thereof, the component is a hydroprocessing reactor which includes a particulate bed and the particulate bed is comprised of catalyst particles. In yet a further embodiment thereof, the catalyst particles are comprised of a hydrodesulfurization catalyst, a hydrodenitrogenation catalyst, a hydrodeoxygenation catalyst, a hydrocracking catalyst, a hydroreforming catalyst, a hydroisomerization catalyst, or any combination thereof.

Embodiment 23 the system of embodiment 21 or 22, wherein the optical fiber sensor array and the optical signal interrogator include a fiber Bragg grating array based sensing system, a Raman scattering based sensing system, a Rayleigh scattering based sensing system, or a Brillioun scattering based sensing system.

Embodiment 24 the system of embodiments 21, 22 or 23, wherein the heating element includes a resistive heating element and wherein the excitation source is configured to propagate an electrical pulse with a predetermined frequency and predetermined waveform, the electrical pulse corresponding to the at least one heat pulse.

Embodiment 25 the system of embodiments 21, 22, 23, or 24, wherein the heating element is aligned adjacent to the optical fiber sensor array.

Embodiment 26 the system of embodiments 21, 22, 23, or 24, wherein the heating element is disposed concentrically with the optical fiber sensor array.

Embodiment 27 the system of embodiments 21, 22, 23, 25 or 26, wherein the heating element includes a thermoelectric device and wherein the at least one heat pulse including a cooling pulse.

Embodiment 28 the system of embodiments 21, 22, 23, 24, 25, 26 or 27, wherein the sensing cable further includes an anti-fouling coating to prevent formation of deposits thereon.

Embodiment 29 the system of embodiments 21, 22, 23, 24, 25, 26, 27 or 28, wherein the sensing cable further includes an outer diameter including a metal and mineral insulation material.

Embodiment 30 the system of embodiments 21, 22, 23, 24, 25, 26, 27, 28 or 29, wherein the optical signal interrogator is configured, for each of the plurality of sensor locations, to measure at least a heating temperature measurement during propagation of the heat pulse over the sensor location, a peak temperature measurement, and a cooling temperature measurement after propagation of the heat pulse over the sensor.

Embodiment 31 the system of embodiments 21, 22, 23, 24, 25, 26, 27, 28, 29 or 30, wherein the optical signal interrogator is configured, for each of the plurality of sensor locations, to measure a plurality of temperatures over a period of time upon arrival of the heat pulse at the sensor location.

Embodiment 32 the system of embodiment 31, wherein the control unit is configured, for each temperature profile, to perform a regression of the plurality of temperatures over a logarithm of corresponding measurement times for a predetermined time window in the period of time to generate a slope and an intercept of the regression, wherein the slope and the intercept relate to the flow of the fluid over the sensing cable at the sensor location.

Embodiment 33 the system of embodiment 32, wherein the predetermined time window includes a time window during a heating stage, the heating stage corresponding to a period of time during propagation of the heat pulse over the sensor location or a time window during a cooling stage, the cooling stage corresponding to a period of time after propagation of the heat pulse over the sensor.

Embodiment 34 the system of embodiments 31, 32 or 33, wherein the control unit is configured, for each temperature profile, to: generate a time derivative by calculating a derivative of the plurality of temperature measurements with respect to time; apply a transform to the time derivative to generate a complex spectrum; and determine an amplitude and a phase of the complex spectrum, wherein the amplitude and the phase of the complex spectrum relate to the flow of the fluid over the sensing cable at the sensor location.

Embodiment 35 the system of embodiments 34, wherein the control unit is further configured, for each temperature profile, to: generate a frequency derivative spectrum by calculating the derivative of the complex spectrum with respect to frequency; and determine an amplitude and a phase of the frequency derivative spectrum, wherein the amplitude and the phase of the frequency derivative spectrum relate to the flow of the fluid over the sensing cable at the sensor location.

Embodiment 36 the system of embodiments 21, 22, 23, 24, 25, 26, 27, 28, 29, 30, 31, 32, 33, 34 or 35, wherein the control unit is further configured to detect a misdistribution condition in the component by monitoring the temperature profile corresponding to each of the plurality of sensor locations, and comparing the monitored temperature profiles to predetermined temperature profiles corresponding to a desired operation condition.

Embodiment 37 the system of embodiments 21, 22, 23, 24, 25, 26, 27, 28, 29, 30, 31, 32, 33, 34, 35 or 36, wherein the control unit is further configured to detect a misdistribution condition in the component by monitoring a first temperature profile corresponding to each of the plurality of sensor locations and at least a second temperature profile corresponding to each of the plurality of sensor locations, and comparing the first and second temperature profiles to detect a change in operation condition.

Embodiment 38 the system of embodiments 21, 22, 23, 24, 25, 26, 27, 28, 29, 30, 31, 32, 33, 34, 35, 36 or 37, wherein the sensing cable is disposed in a grid configuration within the component, and wherein the control unit is further configured to generate a multi-dimensional flow distribution based on the temperature profile corresponding to each sensor location.

Embodiment 39 the system of embodiments 21, 22, 23, 24, 25, 26, 27, 28, 29, 30, 31, 32, 33, 34, 35, 36, 37 or 38, wherein the sensing cable further includes a plurality of sensing cables, wherein each of the plurality of sensing cables is disposed within different layers of the component, and wherein the control unit is further configured to generate a multi-dimensional flow distribution based on the temperature profile corresponding to each sensor location.

Embodiment 40 the system of embodiments 21, 22, 23, 24, 25, 26, 27, 28, 29, 30, 31, 32, 33, 34, 35, 36, 37, 39, 39 or 40, wherein the component has an operating temperature between cryogenic temperatures and approximately 1000° C., wherein the sensing cable has a diameter of less than 2 mm, and wherein the optical signal interrogator is configured to measure the temperature profile at a spatial resolution less than 1 mm.

While the disclosed subject matter is described herein in terms of certain exemplary embodiments, those skilled in the art will recognize that various modifications and improvements can be made to the disclosed subject matter without departing from the scope thereof. Moreover, although individual features of one embodiment of the disclosed subject matter can be discussed herein or shown in the drawings of the one embodiment and not in other embodiments, it should be apparent that individual features of one embodiment can be combined with one or more features of another embodiment or features from a plurality of embodiments.

In addition to the specific embodiments claimed below, the disclosed subject matter is also directed to other embodiments having any other possible combination of the dependent features claimed below and those disclosed above. As such, the particular features presented in the dependent claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

What is claimed is:

1. A method for determining the flow distribution of a fluid through a component, comprising:
   providing within a component a sensing cable including an optical fiber sensor array aligned with a heating element;
   propagating at least one heat pulse through the heating element along at least a portion of the sensing cable to affect an exchange of thermal energy between the heating element and the fluid exposed to the sensing cable;
   measuring, over time, a temperature profile of the sensing cable corresponding to the heat pulse at each of a plurality of sensor locations on the optical fiber sensor array; and
   determining a flow of the fluid by determining one or more properties of the fluid exposed to the sensing cable at each of the plurality of sensor locations based on the temperature profile corresponding thereto,
   wherein the component is a hydroprocessing reactor which includes a particulate bed and the particulate bed is comprised of catalyst particles.

2. The method of claim 1, wherein the catalyst particles are comprised of a hydrodesulfurization catalyst, a hydrodenitrogenation catalyst, a hydrodeoxygenation catalyst, a hydrocracking catalyst, a hydroreforming catalyst, a hydroisomerization catalyst, or any combination thereof.

3. The method of claim 1, wherein measuring, over time, the temperature profile includes measuring using fiber Bragg grating array based sensing, Raman scattering based sensing, Rayleigh scattering based sensing, or Brillioun scattering based sensing.

4. The method of claim 1, wherein the heating element includes a resistive heating element and wherein propagating the at least one heat pulse includes applying an electrical pulse with a predetermined frequency and predetermined waveform.

5. The method of claim 1, wherein propagating at least one heat pulse through the heating element includes propagating the at least one heat pulse through a heating element aligned adjacent to the optical fiber sensor array.

6. The method of claim 1, wherein propagating at least one heat pulse through the heating element includes propagating the at least one heat pulse through a heating element disposed concentrically with the optical fiber sensor array.

7. The method of claim 1, wherein the heating element includes a thermoelectric device and wherein propagating at least one heat pulse through the heating element includes propagating a cooling pulse.

8. The method of claim 1, further comprising coating the sensing cable with an anti-fouling coating to prevent formation of deposits thereon.

9. The method of claim 1, wherein the sensing cable further includes an outer diameter including a metal and mineral insulation material.

10. The method of claim 1, wherein measuring the temperature profile corresponding to the heat pulse at each of the plurality of sensor locations includes, for each sensor location, measuring at least a heating temperature measurement during propagation of the heat pulse over the sensor location, a peak temperature measurement, and a cooling temperature measurement after propagation of the heat pulse over the sensor.

11. The method of claim 1, wherein measuring the temperature profile corresponding to the heat pulse at each of the plurality of sensor locations includes, for each sensor location, measuring a plurality of temperatures over a period of time upon arrival of the heat pulse at the sensor location.

12. The method of claim 11, wherein determining the flow of the fluid includes, for each temperature profile, performing a regression of the plurality of temperatures over a logarithm of corresponding measurement times for a predetermined time window in the period of time to generate a slope and an intercept of the regression, wherein the slope and the intercept relate to the flow of the fluid over the sensing cable at the sensor location.

13. The method of claim 12, wherein the predetermined time window includes a time window during a heating stage, the heating stage corresponding to a period of time during propagation of the heat pulse over the sensor location or a time window during a cooling stage, the cooling stage corresponding to a period of time after propagation of the heat pulse over the sensor.

14. The method of claim 11, wherein determining the flow of the fluid includes, for each temperature profile:
generating a time derivative by calculating a derivative of the plurality of temperature measurements with respect to time; applying a transform to the time derivative to generate a complex spectrum; and
determining an amplitude and a phase of the complex spectrum, wherein the amplitude and the phase of the complex spectrum relate to the flow of the fluid over the sensing cable at the sensor location.

15. The method of claim 14, wherein determining the flow of the fluid further includes, for each temperature profile:
generating a frequency derivative spectrum by calculating the derivative of the complex spectrum with respect to frequency; and
determining an amplitude and a phase of the frequency derivative spectrum, wherein the amplitude and the phase of the frequency derivative spectrum relate to the flow of the fluid over the sensing cable at the sensor location.

16. The method of claim 1, wherein determining the flow of the fluid further includes detecting a misdistribution condition in the component by monitoring the temperature profile corresponding to each of the plurality of sensor locations, and comparing the monitored temperature profiles to predetermined temperature profiles corresponding to a desired operation condition.

17. The method of claim 1, wherein determining the flow of the fluid further includes detecting a misdistribution condition in the component by monitoring a first temperature profile corresponding to each of the plurality of sensor locations and at least a second temperature profile corresponding to each of the plurality of sensor locations, and comparing the first and second temperature profiles to detect a change in operation condition.

18. The method of claim 1, wherein the sensing cable is disposed in a grid configuration within the component, the method further comprising generating a multi-dimensional flow distribution based on the temperature profile corresponding to each sensor location.

19. A system for determining the flow distribution of a fluid through a component, comprising:
a sensing cable including an optical fiber sensor array aligned with a heating element disposed in the component, the optical fiber sensor array having a plurality of sensor locations;
an excitation source coupled with the heating element and configured to propagate at least one heat pulse through the heating element along at least a portion of the sensing cable to affect an exchange of thermal energy between the heating element and the fluid exposed to the sensing cable;
an optical signal interrogator coupled with the optical fiber sensor array and adapted to receive a signal from each of the plurality of sensor locations and configured to measure, over time, a temperature profile of the sensing cable corresponding to the heat pulse at each of the plurality of sensor locations on the optical fiber sensor array; and
a control unit, coupled with the heating element and the optical signal interrogator, to determine a flow of the fluid by determining one or more properties of the fluid exposed to the sensing cable at each of the plurality of sensor locations based on the temperature profile corresponding thereto,
wherein the component is a hydroprocessing reactor which includes a particulate bed and the particulate bed is comprised of catalyst particles.

20. The system of claim 19, wherein the catalyst particles are comprised of a hydrodesulfurization catalyst, a hydrodenitrogenation catalyst, a hydrodeoxygenation catalyst, a hydrocracking catalyst, a hydroreforming catalyst, a hydroisomerization catalyst, or any combination thereof.

21. The system of claim 19, wherein the optical fiber sensor array and the optical signal interrogator include a fiber Bragg grating array based sensing system, a Raman scattering based sensing system, a Rayleigh scattering based sensing system, or a Brillioun scattering based sensing system.

22. The system of claim 19, wherein the heating element includes a resistive heating element and wherein the excitation source is configured to propagate an electrical pulse with a predetermined frequency and predetermined waveform, the electrical pulse corresponding to the at least one heat pulse.

23. The system of claim 19, wherein the heating element is aligned adjacent to the optical fiber sensor array.

24. The system of claim 19, wherein the heating element is disposed concentrically with the optical fiber sensor array.

25. The system of claim 19, wherein the heating element includes a thermoelectric device and wherein the at least one heat pulse including a cooling pulse.

26. The system of claim 19, wherein the sensing cable further includes an anti-fouling coating to prevent formation of deposits thereon.

27. The system of claim 19, wherein the sensing cable further includes an outer diameter including a metal and mineral insulation material.

28. The system of claim 19, wherein the optical signal interrogator is configured, for each of the plurality of sensor locations, to measure at least a heating temperature measurement during propagation of the heat pulse over the sensor location, a peak temperature measurement, and a cooling temperature measurement after propagation of the heat pulse over the sensor.

29. The system of claim 19, wherein the optical signal interrogator is configured, for each of the plurality of sensor locations, to measure a plurality of temperatures over a period of time upon arrival of the heat pulse at the sensor location.

30. The system of claim 29, wherein the control unit is configured, for each temperature profile, to perform a regression of the plurality of temperatures over a logarithm of corresponding measurement times for a predetermined time window in the period of time to generate a slope and an intercept of the regression, wherein the slope and the intercept relate to the flow of the fluid over the sensing cable at the sensor location.

31. The system of claim 30, wherein the predetermined time window includes a time window during a heating stage, the heating stage corresponding to a period of time during propagation of the heat pulse over the sensor location or a time window during a cooling stage, the cooling stage corresponding to a period of time after propagation of the heat pulse over the sensor.

32. The system of claim 29, wherein the control unit is configured, for each temperature profile, to:
generate a time derivative by calculating a derivative of the plurality of temperature measurements with respect to time; apply a transform to the time derivative to generate a complex spectrum; and
determine an amplitude and a phase of the complex spectrum, wherein the amplitude and the phase of the complex spectrum relate to the flow of the fluid over the sensing cable at the sensor location.

33. The system of claim 32, wherein the control unit is further configured, for each temperature profile, to:
generate a frequency derivative spectrum by calculating the derivative of the complex spectrum with respect to frequency; and
determine an amplitude and a phase of the frequency derivative spectrum, wherein the amplitude and the phase of the frequency derivative spectrum relate to the flow of the fluid over the sensing cable at the sensor location.

34. The system of claim 19, wherein the control unit is further configured to detect a misdistribution condition in the component by monitoring the temperature profile corresponding to each of the plurality of sensor locations, and comparing the monitored temperature profiles to predetermined temperature profiles corresponding to a desired operation condition.

35. The system of claim 19, wherein the control unit is further configured to detect a misdistribution condition in the component by monitoring a first temperature profile corresponding to each of the plurality of sensor locations and at least a second temperature profile corresponding to each of the plurality of sensor locations, and comparing the first and second temperature profiles to detect a change in operation condition.

36. The system of claim 19, wherein the sensing cable is disposed in a grid configuration within the component, and wherein the control unit is further configured to generate a multi-dimensional flow distribution based on the temperature profile corresponding to each sensor location.

37. The system of claim 19, wherein the sensing cable further includes a plurality of sensing cables, wherein each of the plurality of sensing cables is disposed within different layers of the component, and wherein the control unit is further configured to generate a multi-dimensional flow distribution based on the temperature profile corresponding to each sensor location.

* * * * *